United States Patent
Stefinovic et al.

(10) Patent No.: US 12,043,590 B2
(45) Date of Patent: Jul. 23, 2024

(54) CO-CRYSTALS COMPRISING LEVOTHYROXINE AND A DICARBOXYLIC ACID

(71) Applicant: Sandoz AG, Basel (CH)

(72) Inventors: Marijan Stefinovic, Kundl (AT); Dennis Dimo Enkelmann, Innsbruck (AT); Ulrich Griesser, Innsbruck (AT); Thomas Gelbrich, Innsbruck (AT)

(73) Assignee: Sandoz AG, Basel (CH)

( * ) Notice: Subject to any disclaimer, the term of this patent is extended or adjusted under 35 U.S.C. 154(b) by 638 days.

(21) Appl. No.: 17/285,653

(22) PCT Filed: Oct. 16, 2019

(86) PCT No.: PCT/EP2019/078084
§ 371 (c)(1),
(2) Date: Apr. 15, 2021

(87) PCT Pub. No.: WO2020/079079
PCT Pub. Date: Apr. 23, 2020

(65) Prior Publication Data
US 2021/0395186 A1    Dec. 23, 2021

(30) Foreign Application Priority Data

Oct. 17, 2018  (EP) .................................. 18200869
Oct. 2, 2019   (EP) .................................. 19201020

(51) Int. Cl.
C07C 229/36  (2006.01)
C07C 55/02   (2006.01)

(52) U.S. Cl.
CPC ............ C07C 229/36 (2013.01); C07C 55/02 (2013.01); *C07B 2200/13* (2013.01)

(58) Field of Classification Search
CPC ..... C07C 229/36; C07C 55/02; C07C 59/255; C07C 59/08; C07B 2200/13; A61P 5/14; A61K 31/198
See application file for complete search history.

(56) References Cited

U.S. PATENT DOCUMENTS 7,858,663 B1 * 12/2010 Bristol ................. A61K 31/195
                                                           514/561
2018/0064669 A1   3/2018 Tengler

FOREIGN PATENT DOCUMENTS

| CA | 2771564 C       | 8/2018  |              |
|----|-----------------|---------|--------------|
| CN | 103649091 A     | 3/2014  |              |
| CN | 108250219 A     | 7/2018  |              |
| WO | 9520954 A1      | 8/1995  |              |
| WO | 2009052391 A1   | 4/2009  |              |
| WO | 2012136553 A1   | 10/2012 |              |
| WO | WO-2017077476 A1 * | 5/2017 | ........... A61K 31/198 |

OTHER PUBLICATIONS

Meanwell, The Emerging Utility of Co-Crystals in Drug Discovery and Development, (Annual Reports in Medicinal Chemistry, 43, p. 373-404). (Year: 2008).*
Schultheiss et al. Pharmaceutical cocrystals and Their Physicochemical Properties, (Crystal Growth & Design, 9, 2950-2967). (Year : 2009).*
Hamad, Lee, et al., Pharm Dev Technol, 20 (3), 2015, pp. 314-319.
International Search Report and Written Opinion for PCT/EP2019/078084, dated Apr. 23, 2020, 10 pages.
Parsons, Simon, et al., Acta Cryst, B69, 2013, pp. 249-259.
Pecharsky, et al., Fundamentals of powder diffraction and structural characterization of materials, 2005, Springer, p. 3.
Sarkar,Anindita, et al., Journal of Pharmaceutical Sciences, 104, 2015, pp. 98-105.
Sheldrick, George M., Acta Cryst, A71, 2015, pp. 3-8.
Sheldrick, George M., Acta Cryst, C71, 2015, pp. 3-8.
Vioglio, Paulo Cerreia, et al., Advanced Delivery Review, 117, 2017, pp. 86-110.
Armando Valencia Hernández, Mexican Institute of Industrial Property, Notice, Mexico City, Nov. 28, 2023.
Dario Braga, Fabrizia Grepioni, Lucia Maini and Marco Polito, Crystal Polymorphism and Multiple Crystal Forms, Published Feb. 25, 2009, Bologna, Italy.
Mino R. Caira, Crystalline Polymorphism of Organic Compounds, Department of Chemistry, University of Cape Town, Rondebosch 7700, South Africa, vol. 198, 1998.
Rolf Hilfiker, Fritz Blatter and Markus Von Raumer, Relevance of Solid-state Properties for Pharmaceutical Products, Weinheim, 2006.

* cited by examiner

*Primary Examiner* — Matthew P Coughlin
*Assistant Examiner* — Meghan C Heasley
(74) *Attorney, Agent, or Firm* — Luedeka Neely, P.C.

(57) ABSTRACT

The present invention relates to co-crystals comprising levothyroxine and a dicarboxylic acid, preferably L-tartaric acid or oxalic acid, and processes for the preparation thereof. Furthermore, the invention relates to a pharmaceutical composition comprising a co-crystal of the present invention, preferably the co-crystal comprising levothyroxine and L-tartaric acid or oxalic acid, and at least one pharmaceutically acceptable excipient. The pharmaceutical composition of the present invention can be used as a medicament, in particular for the treatment of hypothyroidism.

27 Claims, 15 Drawing Sheets

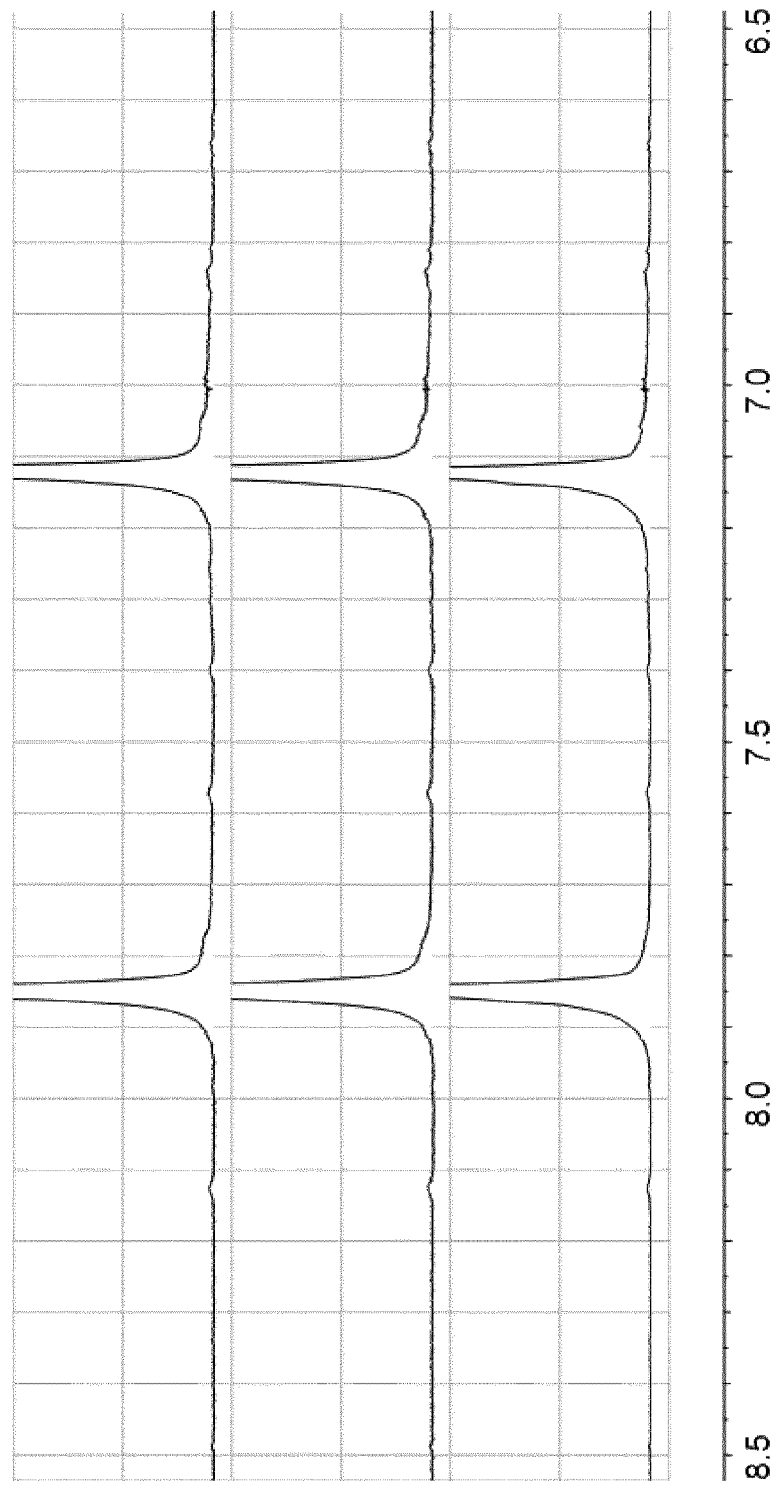

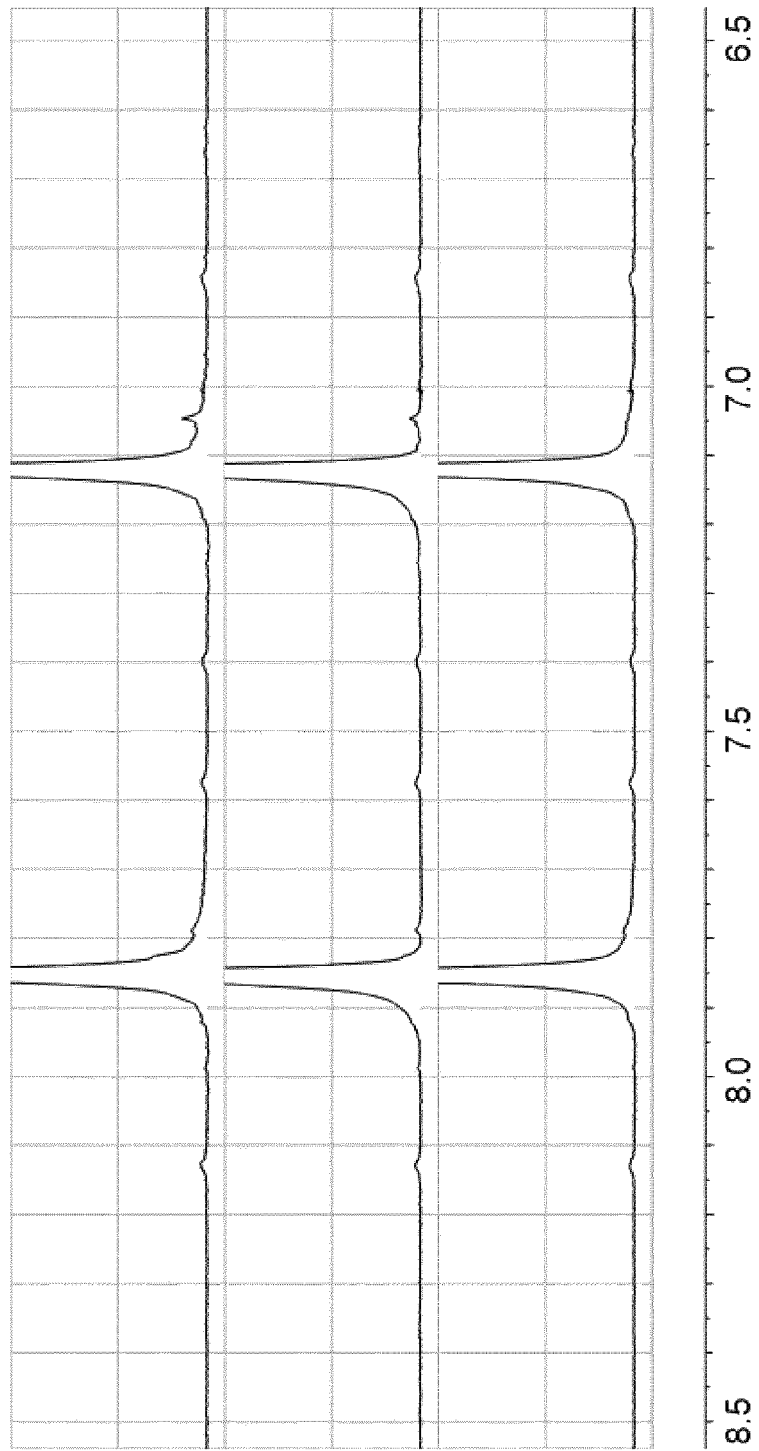

CO-CRYSTALS COMPRISING LEVOTHYROXINE AND A DICARBOXYLIC ACID

This application is a Section 371 national phase entry of PCT application PCT/EP2019/078084, filed Oct. 16, 2019. This application also claims the benefit of the earlier filing date of European patent application 18200869.8, filed Oct. 17, 2018, and European patent application 19201020.5, filed Oct. 2, 2019.

FIELD OF THE INVENTION

The present invention relates to co-crystals comprising levothyroxine and a dicarboxylic acid, preferably L-tartaric acid or oxalic acid, and processes for the preparation thereof. Furthermore, the invention relates to a pharmaceutical composition comprising a co-crystal of the present invention, preferably the co-crystal comprising levothyroxine and L-tartaric acid or oxalic acid, and at least one pharmaceutically acceptable excipient. The pharmaceutical composition of the present invention can be used as a medicament, in particular for the treatment of hypothyroidism.

BACKGROUND OF THE INVENTION

Levothyroxine is mainly used as replacement therapy in the treatment of hypothyroidism. It is a synthetic thyroid hormone that exerts the same physiologic effect as endogenous levothyroxine produced in the thyroid gland, thereby maintaining normal levothyroxine levels when deficiency is present.

It is also indicated for pituitary TSH suppression in the treatment or prevention of various types of euthyroid goiters.

By far the most popular levothyroxine formulations are immediate release tablets. Marketed levothyroxine sodium tablets contain the pentahydrate form of the active agent. Levothyroxine sodium pentahydrate can be represented by the chemical structure as depicted in formula A

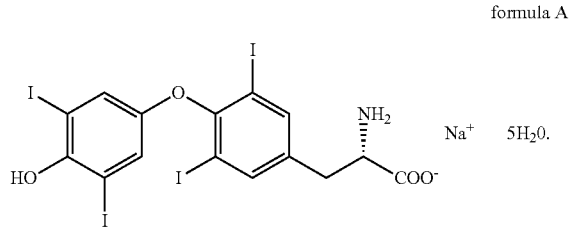

formula A

Levothyroxine sodium tablets are low dose medications with different strengths ranging from 25 to 300 micrograms. Besides the low dose levothyroxine sodium is also classified as a narrow therapeutic index (NTI) drug. NTI drugs have less than a 2-fold difference in the minimum toxic concentrations and minimum effective concentrations in the blood, and safe and effective use of the drug products requires careful dosage titration and patient monitoring. As levothyroxine sodium is a low dose, NTI medication, normally acceptable levels of chemical degradation, uniformity or loss experienced during manufacturing may lead to sub or super potency in levothyroxine sodium tablets, which may have adverse clinical consequences, affecting both the efficacy and the safety of the product. Consequences of over- or under-treatment can be, among others, effects on growth and development, cardiovascular function, bone metabolism, reproductive function, cognitive function, emotional state, gastrointestinal function, and on glucose and lipid metabolism.

Since their market introduction in the 1950's levothyroxine sodium tablets have been recalled many times by several different manufacturers. The basis for most of the recalls was chemical instability of the levothyroxine sodium pentahydrate drug substance, resulting in failures to meet content uniformity and potency specifications prior to expiration dates.

In particular, it was found by the inventors of the present invention that commercial levothyroxine sodium pentahydrate is physically and chemically unstable when subjected to pressure and/or temperature stress, which is critical for pharmaceutical processing which usually involves such conditions.

The chemical instability of levothyroxine sodium pentahydrate is also subject-matter of scientific publications. For example, Mazen Lee Hamad et al. *"Impact of hydration state and molecular oxygen on the chemical stability of levothyroxine sodium" Pharm Dev Technol*, 2015; 20(3): 314-319 suggest that exposure of levothyroxine sodium pentahydrate to dry conditions in the presence of molecular oxygen leads to significant degradation. Consequently, formulating levothyroxine sodium pentahydrate with certain excipients, in particular hygroscopic excipients, could induce chemical degradation.

For many patients, levothyroxine is a lifesaving medication with no substitute and once patients start taking levothyroxine, most will continue requiring this medicine for the remainder of their lives. There is thus a need for levothyroxine tablets having high product quality and ensuring high safety and efficacy standards for patients relying on levothyroxine substitution.

SUMMARY OF THE INVENTION

The present invention is aiming at providing an improved levothyroxine drug product. This is achieved by providing a physically and chemically stable physical form of levothyroxine which preserves reliable potency over the whole shelf-life of a levothyroxine tablet. In particular, the present invention provides an improved solid state form of levothyroxine e.g. a crystalline form of levothyroxine which is chemically and physically more stable than the levothyroxine sodium pentahydrate, which is the currently marketed form of levothyroxine.

The invention provides co-crystals comprising levothyroxine and a dicarboxylic acid, preferably a $C_{2-8}$ dicarboxylic acid, more preferably a $C_{2-6}$ dicarboxylic acid selected from the group consisting of adipic acid, aspartic acid, fumaric acid, glutamic acid, glutaric acid, maleic acid, malic acid, malonic acid, oxalic acid, succinic acid and tartaric acid. In particular, the present invention provides co-crystals comprising levothyroxine and a dicarboxylic acid, preferably a $C_{2-4}$ dicarboxylic acid selected from the group consisting of aspartic acid, fumaric acid, maleic acid, malic acid, malonic acid, oxalic acid, succinic acid and tartaric acid. In another embodiment, the invention relates to co-crystals comprising levothyroxine and a dicarboxylic acid, preferably a $C_4$ dicarboxylic acid selected from the group consisting of aspartic acid, fumaric acid, maleic acid, malic acid, succinic acid and tartaric acid. More preferably, the invention relates to a co-crystal comprising levothyroxine and L-tartaric acid or oxalic acid and most preferably the invention relates to a co-crystal comprising levothyroxine and L-tartaric acid.

The co-crystals of the present invention, in particular the co-crystal comprising levothyroxine and L-tartaric acid or oxalic acid are chemically and physically more stable under various conditions compared to commercial levothyroxine sodium pentahydrate.

For example, they are more stable when subjected to dry conditions in the presence of molecular oxygen, whereas levothyroxine sodium pentahydrate dehydrates and subsequently decomposes very quickly under the same conditions. This is of particular relevance, since formulating levothyroxine sodium pentahydrate or the levothyroxine co-crystal of the present invention with hygroscopic excipients is analogous to subjecting the drug substance to dry conditions. Also drying conditions have to be chosen carefully for levothyroxine sodium pentahydrate, while there is no need for special care for the co-crystals of the present invention.

Moreover, the co-crystals of the present invention, in particular the co-crystals comprising levothyroxine and L-tartaric acid or oxalic acid are physically and chemically more stable compared to commercial levothyroxine sodium pentahydrate when exposed to pressure. While compression e.g. during the tableting process has a negative influence on the chemical and physical stability of levothyroxine sodium pentahydrate, the co-crystals of the present invention remain both physically and chemically stable.

Last but not least, the co-crystals of the present invention, in particular the co-crystal comprising levothyroxine and L-tartaric acid are also more stable against temperature stress compared to levothyroxine sodium pentahydrate. Several processes during tablet manufacture like milling and drying include the evolution of heat. Hence, it is of great importance that the drug substance remains stable upon temperature stress.

While special care has to be taken during manufacture and when formulating, packaging and storing levothyroxine sodium pentahydrate, the co-crystals of the present invention can be manufactured with standardized methods and equipment due to their improved physical and chemical stability. The levothyroxine co-crystals of the present invention therefore allow for the straightforward manufacture of a safe and efficacious levothyroxine medicament having constant potency during the whole shelf-life.

Abbreviations

PXRD powder X-ray diffractogram
SXRD single crystal X-ray diffraction
DSC differential scanning calorimetry
TGA thermogravimetric analysis
NMR nuclear magnetic resonance
RT room temperature
RH relative humidity
GC gas chromatography
MS mass spectrometry
rpm rotations per minute
EtOH ethanol Definitions The term "levothyroxine" (also known as "L-thyroxine, tetraiodothyronine and "$T_4$") as used herein refers to (S)-2-amino-3-(4-(4-hydroxy-3,5-diiodophenoxy)-3,5-diiodophenyl)propanoic acid or O-(4-hydroxy-3,5-diiodophenyl)-3,5-diiodo-L-thyronine. Levothyroxine can be represented by the chemical structure depicted in formula B

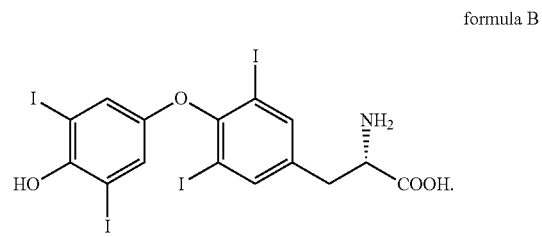 [SMILES: N[C@@H](Cc1cc(I)c(Oc2cc(I)c(O)c(I)c2)c(I)c1)C(=O)O]

formula B

In the course of the present invention the term "levothyroxine" also encompasses the zwitterionic form of the molecule as represented by the chemical structure depicted in formula C

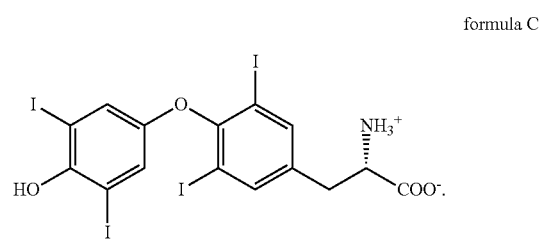

formula C

The term "co-crystal" as used herein refers to a crystalline material composed of two or more different molecular and/or ionic compounds in the same crystal lattice that are associated by nonionic and noncovalent bonds, wherein at least two of the individual molecular and/or ionic compounds are solids at room temperature.

The term "hydrate" as used herein, refers to a crystalline solid where either water is cooperated in or accommodated by the crystal structure e.g. is part of the crystal structure or entrapped into the crystal (water inclusions). Thereby, water can be present in a stoichiometric or non-stoichiometric amount. When water is present in stoichiometric amount, the hydrate may be referred to by adding greek numeral prefixes. For example, a hydrate may be referred to as a monohydrate or as a pentahydrate depending on the water/compound stoichiometry. The water content can be measured, for example, by Karl-Fischer-Coulometry.

The terms "dehydrating" or "dehydration" as used herein, describe the at least partial removal of water from the crystal structure of the host molecule.

The term "solvate" as used herein, refers to a crystalline solid where either one or more organic solvent(s) is/are cooperated in or accommodated by the crystal structure e.g. is/are part of the crystal structure or entrapped into the crystal (solvent inclusions). Thereby, the one or more organic solvent(s) can be present in a stoichiometric or non-stoichiometric amount. When the one or more organic solvent(s) is/are present in stoichiometric amount(s), the solvate may be referred to by adding greek numeral prefixes. For example, a solvate may be referred to as a hemisolvate or as a monosolvate depending on the solvent(s)/compound stoichiometry. The solvent content can be determined, for example, by GC, $^1$H-NMR, SXRD and/or TGA/MS.

As used herein the term "room temperature" refers to a temperature in the range of from 20 to 30° C.

As used herein, the term "dicarboxylic acid" refers to straight-chained or branched, saturated or unsaturated, substituted or unsubstituted dicarboxylic acids.

As used herein, the term "$C_{2-8}$ dicarboxylic acid" refers to straight-chained or branched, saturated or unsaturated, substituted or unsubstituted dicarboxylic acids having from 2 to 8 carbon atoms, including but not limited to adipic acid, aspartic acid, fumaric acid, glutamic acid, glutaric acid, maleic acid, malic acid, malonic acid, oxalic acid, succinic acid and tartaric acid.

As used herein, the term "$C_{2-6}$ dicarboxylic acid" refers to straight-chained or branched, saturated or unsaturated, substituted or unsubstituted dicarboxylic acids having from 2 to 6 carbon atoms, including but not limited to adipic acid, aspartic acid, fumaric acid, glutamic acid, glutaric acid, maleic acid, malic acid, malonic acid, oxalic acid, succinic acid and tartaric acid.

As used herein, the term "$C_{2-4}$ dicarboxylic acid" refers to straight-chained or branched, saturated or unsaturated, substituted or unsubstituted dicarboxylic acids having from 2 to 4 carbon atoms, including but not limited to aspartic acid, fumaric acid, maleic acid, malic acid, malonic acid, oxalic acid, succinic acid and tartaric acid.

As used herein, the term "$C_4$ dicarboxylic acid" refers to straight-chained or branched, saturated or unsaturated, substituted or unsubstituted dicarboxylic acid having 4 carbon atoms, including but not limited to aspartic acid, fumaric acid, maleic acid, malic acid, succinic acid and tartaric acid.

As used herein, the term "measured at a temperature in the range of from 20 to 30° C." refers to a measurement under standard conditions. Typically, standard conditions mean a temperature in the range of from 20 to 30° C., i.e. at room temperature. Standard conditions can mean a temperature of about 22° C. Typically, standard conditions can additionally mean a measurement under 20-70% relative humidity.

The term "reflection" with regard to powder X-ray diffraction as used herein, means peaks in an X-ray diffractogram, which are caused at certain diffraction angles (Bragg angles) by constructive interference from X-rays scattered by parallel planes of atoms in solid material, which are distributed in an ordered and repetitive pattern in a long-range positional order. Such a solid material is classified as crystalline material, whereas amorphous material is defined as solid material, which lacks long-range order and only displays short-range order, thus resulting in broad scattering. According to literature, long-range order e.g. extends over approximately 100 to 1000 atoms, whereas short-range order is over a few atoms only (see *Fundamentals of Powder Diffraction and Structural Characterization of Materials*" by Vitalij K Pecharsky and Peter Y. Zavalij, Kluwer Academic Publishers, 2003, page 3).

The term "essentially the same" with reference to powder X-ray diffraction means that variabilities in reflection positions and relative intensities of the reflections are to be taken into account. For example, a typical precision of the 2-Theta values is in the range of ±0.2° 2-Theta, preferably in the range of ±0.1° 2-Theta. Thus, a reflection that usually appears at 3.7° 2-Theta for example can appear between 3.5° and 3.9° 2-Theta, preferably between 3.6 and 3.8° 2-Theta on most X-ray diffractometers under standard conditions. Furthermore, one skilled in the art will appreciate that relative reflection intensities will show inter-apparatus variability as well as variability due to degree of crystallinity, preferred orientation, sample preparation and other factors known to those skilled in the art and should be taken as qualitative measure only.

The term "essentially the same" with reference to infrared spectrometry means that variabilities in peak positions and relative intensities of the peaks are to be taken into account. For example, a typical precision of the wavenumber values is in the range of ±4 cm$^{-1}$, preferably in the range of ±2 cm$^{-1}$. Thus, a peak at 1769 cm$^{-1}$ for example can appear between 1765 and 1773 cm$^{-1}$, preferably between 1767 and 1771 cm$^{-1}$ on most infrared spectrometers under standard conditions. Peak intensities can be derived from according figures, but one skilled in the art will appreciate that differences in peak intensities due to degree of crystallinity, sample preparation, measurement method and other factors can also occur in infrared spectroscopy. Peak intensities should therefore be taken as qualitative measure only.

The term "essentially the same" with reference to Raman spectrometry means that variabilities in peak positions and relative intensities of the peaks have to be taken into account. The precision of wavenumber positions may depend on the type of instrument (e.g. benchtop dispersive, benchtop FT or handheld) and is typically in the range of ±4 cm$^{-1}$, preferably in the range of ±2 cm$^{-1}$. Thus, a peak at 1242 cm$^{-1}$ for example can appear between 1238 and 1246 cm$^{-1}$, preferably between 1240 and 1244 cm$^{-1}$ on most Raman spectrometers under standard conditions. Peak intensities can be derived from according figures, but one skilled in the art will appreciate that differences in peak intensities due to degree of crystallinity, sample preparation, measurement method and other factors can also occur in Raman spectroscopy. Peak intensities should therefore be taken as qualitative measure only.

A co-crystal of the present invention, in particular the co-crystals of the present invention comprising levothyroxine and L-tartaric acid or oxalic acid may be referred to herein as being characterized by a powder X-ray diffractogram or an infrared spectrum or a Raman spectrum "as shown in" a figure. The person skilled in the art understands that factors such as variations in instrument type, response and variations in sample directionality, sample concentration, sample purity, sample history and sample preparation may lead to variations, for example relating to the exact reflection or peak positions and intensities. However, a comparison of the graphical data in the figures herein with the graphical data generated for an unknown physical form and the confirmation that two sets of graphical data relate to the same crystal form is well within the knowledge of a person skilled in the art.

As used herein, the term "mother liquor" refers to the solution remaining after crystallization of a solid from said solution.

A "predetermined amount" as used herein with regard to a levothyroxine co-crystal, in particular the co-crystals of the present invention comprising levothyroxine and L-tartaric acid or oxalic acid, refers to the initial amount of the levothyroxine co-crystal, in particular the co-crystal of the present invention comprising levothyroxine and L-tartaric acid or oxalic acid used for the preparation of a pharmaceutical composition having a desired dosage strength.

As used herein, the term "effective amount" in conjunction with a levothyroxine co-crystal, in particular the co-crystals of the present invention comprising levothyroxine and L-tartaric acid or oxalic acid encompasses an amount of the levothyroxine co-crystal, in particular the co-crystal of the present invention comprising levothyroxine and L-tartaric acid or oxalic acid which causes the desired therapeutic or prophylactic effect.

As used herein, the term "about" means within a statistically meaningful range of a value. Such a range can be within an order of magnitude, typically within 10%, more typically within 5%, even more typically within 1% and most typically within 0.1% of the indicated value or range. Sometimes, such a range can lie within the experimental error, typical of standard methods used for the measurement and/or determination of a given value or range.

The term "pharmaceutically acceptable excipient" as used herein refers to substances, which do not have a significant pharmacological activity at the given dose and that are added to a pharmaceutical composition in addition to the active pharmaceutical ingredient. Excipients may take the function of vehicle, diluent, release agent, disintegrating agent, dissolution modifying agent, absorption enhancer, stabilizer or a manufacturing aid among others. Excipients may include fillers (diluents), binders, disintegrants, lubricants and glidants.

The terms "filler" or "diluent" as used herein refer to substances that are used to dilute the active pharmaceutical ingredient prior to delivery. Diluents and fillers can also serve as stabilizers.

As used herein the term "binder" refers to substances which bind the active pharmaceutical ingredient and pharmaceutically acceptable excipient together to maintain cohesive and discrete portions.

The terms "disintegrant" or "disintegrating agent" as used herein refers to substances which, upon addition to a solid pharmaceutical composition, facilitate its break-up or disintegration after administration and permits the release of the active pharmaceutical ingredient as efficiently as possible to allow for its rapid dissolution.

The term "lubricant" as used herein refers to substances which are added to a powder blend to prevent the compacted powder mass from sticking to the equipment during tableting or encapsulation process. They aid the ejection of the tablet from the dies and can improve powder flow.

The term "glidant" as used herein refers to substances which are used for tablet and capsule formulations in order to improve flow properties during tablet compression and to produce an anti-caking effect.

BRIEF DESCRIPTION OF THE FIGURES

FIG. 14: illustrates a stack plot of $^1$H-NMR spectra of the co-crystal of the present invention comprising levothyroxine, L-tartaric acid and L-lactic acid of the initial sample (bottom), the sample exposed for 3 weeks (middle) and the sample exposed for 6 weeks (top) to ambient molecular oxygen at 0% RH and 40° C. The x-axis shows the chemical shifts in parts per million (ppm) in the range of 6.5 to 8.5 ppm.

FIG. 15: illustrates a stack plot of $^1$H-NMR spectra of the co-crystal of the present invention comprising levothyroxine and oxalic acid of the initial sample (bottom), the sample exposed for 3 weeks (middle) and the sample exposed for 6 weeks (top) to ambient molecular oxygen at 0% RH and 40° C. The x-axis shows the chemical shifts in parts per million (ppm) in the range of 6.5 to 8.5 ppm.

DETAILED DESCRIPTION OF THE INVENTION

Figure 1:
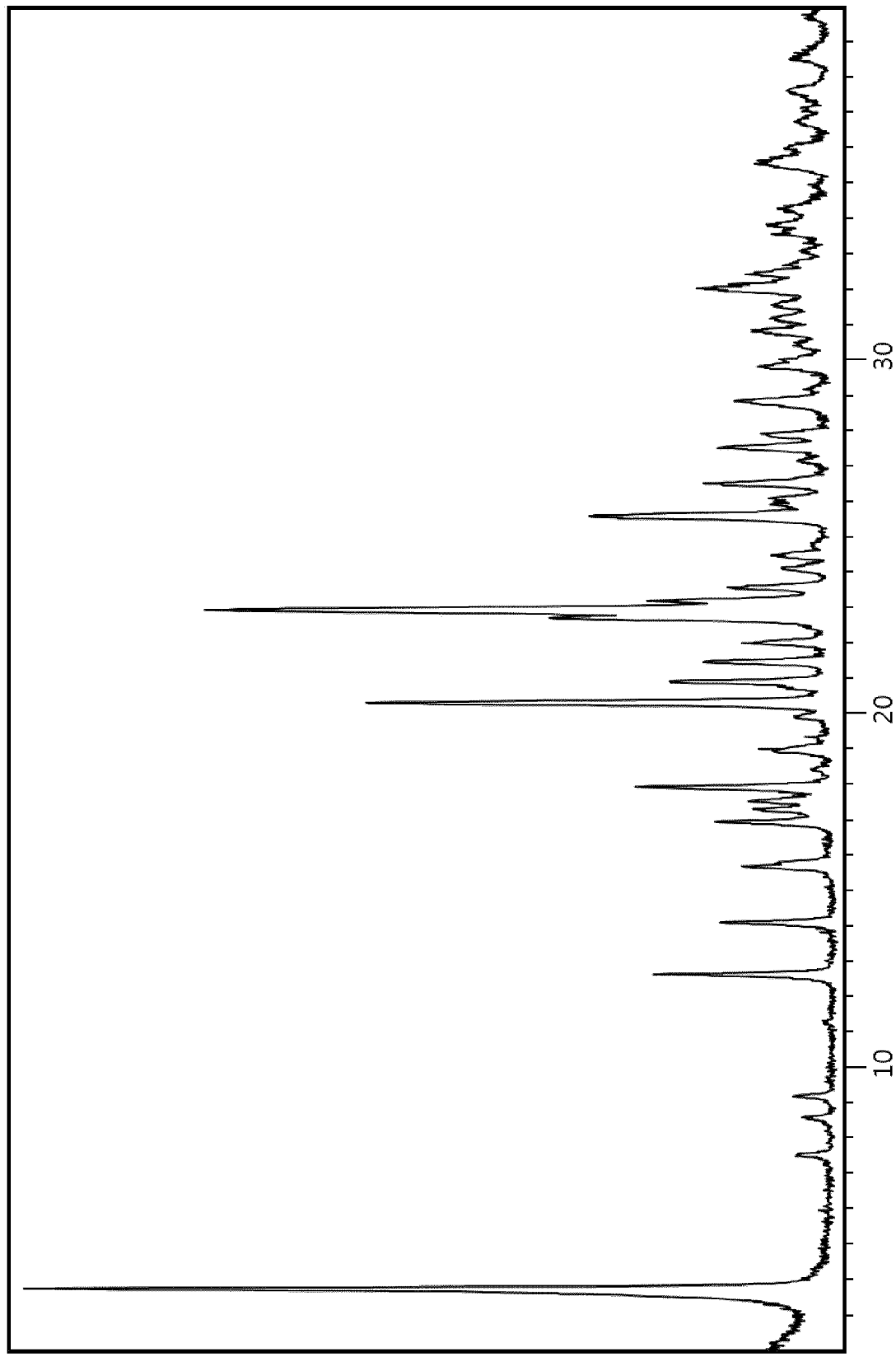
FIG. 1: illustrates a representative PXRD of the co-crystal of the present invention comprising levothyroxine and L-tartaric acid. The x-axis shows the scattering angle in ° 2-Theta, the y-axis shows the relative intensity of the scattered X-ray beam in counts of detected photons.

The present invention relates to a co-crystal comprising levothyroxine and a dicarboxylic acid, preferably a $C_{2-8}$ dicarboxylic acid, more preferably a $C_{2-6}$ dicarboxylic acid, even more preferably a $C_{2-4}$ dicarboxylic acid and most preferably a $C_4$ dicarboxylic acid. The $C_{2-6}$ dicarboxylic acid is preferably selected from the group consisting of adipic acid, aspartic acid, fumaric acid, glutamic acid, glutaric acid, maleic acid, malic acid, malonic acid, oxalic acid, succinic acid and tartaric acid, wherein oxalic acid is particularly preferred and tartaric acid is most preferred. The tartaric acid may be selected from the group consisting of L-tartaric acid, D-tartaric acid and DL-tartaric acid. Most preferably, the tartaric acid is L-tartaric acid.

The molar ratio of levothyroxine and the dicarboxylic acid, preferably the $C_{2-8}$ dicarboxylic acid, more preferably the $C_{2-6}$ dicarboxylic acid even more preferably the $C_{2-4}$ dicarboxylic acid and most preferably the $C_4$ dicarboxylic acid is in the range of from 1.0:0.8-1.2, preferably of from 1.0:0.9-1.1, even more preferably of from 1.00:0.95-1.05 and most preferably the molar ratio is 1.0:1.0. In one embodiment, the molar ratio of levothyroxine and the dicarboxylic acid, preferably the $C_{2-8}$ dicarboxylic acid, more preferably the $C_{2-6}$ dicarboxylic acid even more preferably the $C_{2-4}$ dicarboxylic acid and most preferably the $C_4$ dicarboxylic acid is in the range of from 1.0:1.8-2.2, preferably of from 1.0:1.9-2.1, even more preferably of from 1.00:1.95-2.05 and most preferably the molar ratio is 1.0:2.0.

In a particular preferred embodiment, the invention relates to a co-crystal as described above comprising levothyroxine and L-tartaric acid or oxalic acid.

The co-crystals of the present invention comprising levothyroxine and L-tartaric acid or oxalic acid may be characterized by analytical methods well known in the field of the pharmaceutical industry for characterizing crystalline solids. Such methods comprise, but are not limited to PXRD, SXRD, FTIR, DSC and TGA. The co-crystals of the present invention comprising levothyroxine and L-tartaric acid or oxalic acid may be characterized by one of the aforementioned analytical methods or by combining two or more of them. In particular, the co-crystal of the present invention comprising levothyroxine and L-tartaric acid or oxalic acid may be characterized by any one of the following embodiments or by combining two or more of the following embodiments.

Co-Crystal Comprising Levothyroxine and L-Tartaric Acid

In a first embodiment the invention relates to a co-crystal comprising levothyroxine and L-tartaric acid characterized by having a PXRD comprising reflections at 2-Theta angles of:

(3.7±0.2)°, (20.3±0.2)° and (22.9±0.2)°; or
(3.7±0.2)°, (12.6±0.2)°, (20.3±0.2)° and (22.9±0.2)°; or
(3.7±0.2)°, (12.6±0.2)°, (17.9±0.2)°, (20.3±0.2)° and (22.9±0.2)°; or
(3.7±0.2)°, (12.6±0.2)°, (14.1±0.2)°, (17.9±0.2)°, (20.3±0.2)° and (22.9±0.2)°; or
(3.7±0.2)°, (12.6±0.2)°, (14.1±0.2)°, (17.9±0.2)°, (20.3±0.2)°, (20.9±0.2)° and (22.9±0.2)°; or
(3.7±0.2)°, (12.6±0.2)°, (14.1±0.2)°, (15.7±0.2)°, (17.9±0.2)°, (20.3±0.2)°, (20.9±0.2)° and (22.9±0.2)°; or
(3.7±0.2)°, (12.6±0.2)°, (14.1±0.2)°, (15.7±0.2)°, (16.9±0.2)°, (17.9±0.2)°, (20.3±0.2)°, (20.9±0.2)° and (22.9±0.2)°; or
(3.7±0.2)°, (12.6±0.2)°, (14.1±0.2)°, (15.7±0.2)°, (16.9±0.2)°, (17.9±0.2)°, (20.3±0.2)°, (20.9±0.2)°, (21.4±0.2)° and (22.9±0.2)°, when measured at RT with Cu-Kalpha$_{1,2}$ radiation having a wavelength of 0.15419 nm.

In another embodiment, the invention relates to a co-crystal comprising levothyroxine and L-tartaric acid characterized by having a PXRD comprising reflections at 2-Theta angles of (3.7±0.2)°, (12.6±0.2)°, (17.9±0.2)°, (20.3±0.2)°, (20.9±0.2)°, (21.4±0.2)°, (22.7±0.2)°, (22.9±0.2)°, (23.2±0.2)° and (25.6±0.2)°, when measured at RT with Cu-Kalpha$_{1,2}$ radiation having a wavelength of 0.15419 nm.

In a further embodiment the invention relates to a co-crystal comprising levothyroxine and L-tartaric acid characterized by having a PXRD comprising reflections at 2-Theta angles of:

(3.7±0.1)°, (20.3±0.1)° and (22.9±0.1)°; or
(3.7±0.1)°, (12.6±0.1)°, (20.3±0.1)° and (22.9±0.1)°; or
(3.7±0.1)°, (12.6±0.1)°, (17.9±0.1)°, (20.3±0.1)° and (22.9±0.1)°; or
(3.7±0.1)°, (12.6±0.1)°, (14.1±0.1)°, (17.9±0.1)°, (20.3±0.1)° and (22.9±0.1)°; or
(3.7±0.1)°, (12.6±0.1)°, (14.1±0.1)°, (17.9±0.1)°, (20.3±0.1)°, (20.9±0.1)° and (22.9±0.1)°; or
(3.7±0.1)°, (12.6±0.1)°, (14.1±0.1)°, (15.7±0.1)°, (17.9±0.1)°, (20.3±0.1)°, (20.9±0.1)° and (22.9±0.1)°; or
(3.7±0.1)°, (12.6±0.1)°, (14.1±0.1)°, (15.7±0.1)°, (16.9±0.1)°, (17.9±0.1)°, (20.3±0.1)°, (20.9±0.1)° and (22.9±0.1)°; or
(3.7±0.1)°, (12.6±0.1)°, (14.1±0.1)°, (15.7±0.1)°, (16.9±0.1)°, (17.9±0.1)°, (20.3±0.1)°, (20.9±0.1)°, (21.4±0.1)° and (22.9±0.1)°, when measured at RT with Cu-Kalpha$_{1,2}$ radiation having a wavelength of 0.15419 nm.

In yet another embodiment, the invention relates to a co-crystal comprising levothyroxine and L-tartaric acid characterized by having a PXRD comprising reflections at 2-Theta angles of (3.7±0.1)°, (12.6±0.1)°, (17.9±0.1)°, (20.3±0.1)°, (20.9±0.1)°, (21.4±0.1)°, (22.7±0.1)°, (22.9±0.1)°, (23.2±0.1)° and (25.6±0.1)°, when measured at RT with Cu-Kalpha$_{1,2}$ radiation having a wavelength of 0.15419 nm.

In still another embodiment, the present invention relates to a co-crystal comprising levothyroxine and L-tartaric acid characterized by having a PXRD essentially the same as shown in FIG. 1 of the present invention, when measured at RT with Cu-Kalpha$_{1,2}$ radiation having a wavelength of 0.15419 nm.

In one embodiment, the present invention relates to a co-crystal comprising levothyroxine and L-tartaric acid characterized by having an FTIR spectrum comprising peaks at wavenumbers of:

(3471±4) cm⁻¹, (1769±4) cm⁻¹ and (1221±4) cm⁻¹ or;
(3471±4) cm⁻¹, (1769±4) cm⁻¹, (1586±4) cm⁻¹ and (1221±4) cm⁻¹; or
(3471±4) cm⁻¹, (1769±4) cm⁻¹, (1586±4) cm⁻¹, (1433±4) cm⁻¹ and (1221±4) cm⁻¹; or
(3471±4) cm⁻¹, (1769±4) cm⁻¹, (1586±4) cm⁻¹, (1433±4) cm⁻¹, (1282±4) cm⁻¹ and (1221±4) cm⁻¹; or
(3471±4) cm⁻¹, (1769±4) cm⁻¹, (1586±4) cm⁻¹, (1433±4) cm⁻¹, (1282±4) cm⁻¹, (1221±4) cm⁻¹ and (1128±4) cm⁻¹; or
(3471±4) cm⁻¹, (1769±4) cm⁻¹, (1586±4) cm⁻¹, (1433±4) cm⁻¹, (1282±4) cm⁻¹, (1221±4) cm⁻¹, (1128±4) cm⁻¹ and (822±4) cm⁻¹; or
(3471±4) cm⁻¹, (1769±4) cm⁻¹, (1586±4) cm⁻¹, (1433±4) cm⁻¹, (1282±4) cm⁻¹, (1221±4) cm⁻¹, (1128±4) cm⁻¹, (822±4) cm⁻¹ and (656±4) cm⁻¹; or
(3471±4) cm⁻¹, (3128±4) cm⁻¹, (1769±4) cm⁻¹, (1586±4) cm⁻¹, (1433±4) cm⁻¹, (1282±4) cm⁻¹, (1221±4) cm⁻¹, (1128±4) cm⁻¹, (822±4) cm⁻¹ and (656±4) cm⁻¹,
when measured at RT with a diamond ATR cell.

In another embodiment, the present invention relates to a co-crystal comprising levothyroxine and L-tartaric acid characterized by having an FTIR spectrum comprising peaks at wavenumbers of:
(3471±2) cm⁻¹, (1769±2) cm⁻¹ and (1221±2) cm⁻¹ or;
(3471±2) cm⁻¹, (1769±2) cm⁻¹, (1586±2) cm⁻¹ and (1221±2) cm⁻¹; or
(3471±2) cm⁻¹, (1769±2) cm⁻¹, (1586±2) cm⁻¹, (1433±2) cm⁻¹ and (1221±2) cm⁻¹; or
(3471±2) cm⁻¹, (1769±2) cm⁻¹, (1586±2) cm⁻¹, (1433±2) cm⁻¹, (1282±2) cm⁻¹ and (1221±2) cm⁻¹; or
(3471±2) cm⁻¹, (1769±2) cm⁻¹, (1586±2) cm⁻¹, (1433±2) cm⁻¹, (1282±2) cm⁻¹, (1221±2) cm⁻¹ and (1128±2) cm⁻¹; or
(3471±2) cm⁻¹, (1769±2) cm⁻¹, (1586±2) cm⁻¹, (1433±2) cm⁻¹, (1282±2) cm⁻¹, (1221±2) cm⁻¹, (1128±2) cm⁻¹ and (822±2) cm⁻¹; or
(3471±2) cm⁻¹, (1769±2) cm⁻¹, (1586±2) cm⁻¹, (1433±2) cm⁻¹, (1282±2) cm⁻¹, (1221±2) cm⁻¹, (1128±2) cm⁻¹, (822±2) cm⁻¹ and (656±2) cm⁻¹; or
(3471±2) cm⁻¹, (3128±2) cm⁻¹, (1769±2) cm⁻¹, (1586±2) cm⁻¹, (1433±2) cm⁻¹, (1282±2) cm⁻¹, (1221±2) cm⁻¹, (1128±2) cm⁻¹, (822±2) cm⁻¹ and (656±2) cm⁻¹,
when measured at RT with a diamond ATR cell.

Figure 2:
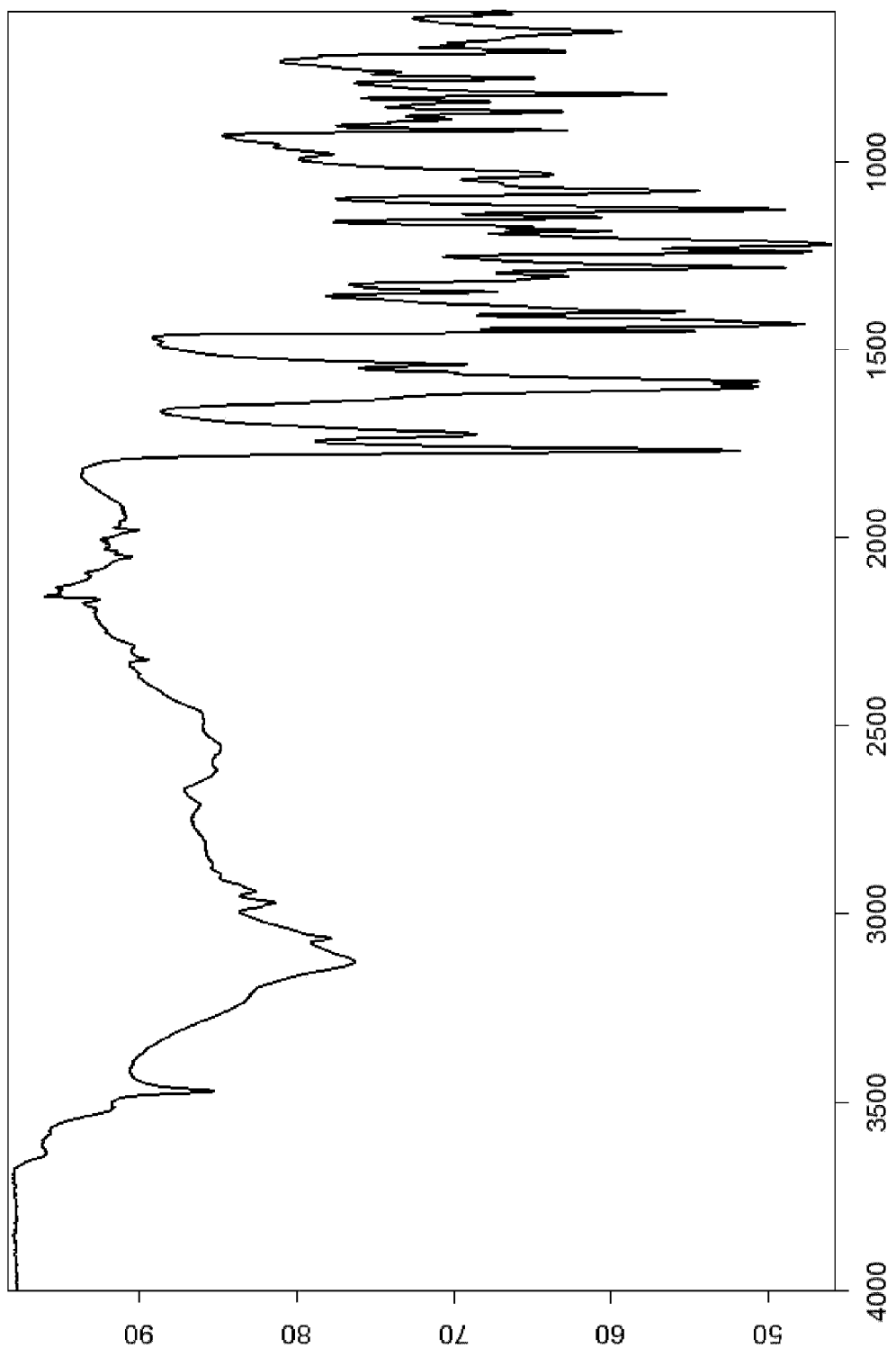
FIG. 2: illustrates a representative FTIR spectrum of the co-crystal of the present invention comprising levothyroxine and L-tartaric acid. The x-axis shows the wavenumbers in $cm^{-1}$, the y-axis shows the relative intensity in percent transmittance.

In yet another embodiment, the present invention relates to a co-crystal comprising levothyroxine and L-tartaric acid characterized by having an FTIR spectrum essentially the same as shown in FIG. 2 of the present invention, when measured at RT with a diamond ATR cell.

In one embodiment, the present invention relates to a co-crystal comprising levothyroxine and L-tartaric acid characterized by having a Raman spectrum comprising peaks at wavenumbers of:
(1242±4) cm⁻¹, (1056±4) cm⁻¹ and (823±4) cm⁻¹; or
(1587±4) cm⁻¹, (1242±4) cm⁻¹, (1056±4) cm⁻¹ and (823±4) cm⁻¹; or
(1732±4) cm⁻¹, (1587±4) cm⁻¹, (1242±4) cm⁻¹, (1056±4) cm⁻¹ and (823±4) cm⁻¹; or
(1732±4) cm⁻¹, (1587±4) cm⁻¹, (1452±4) cm⁻¹, (1242±4) cm⁻¹, (1056±4) cm⁻¹ and (823±4) cm⁻¹; or
(1732±4) cm⁻¹, (1587±4) cm⁻¹, (1452±4) cm⁻¹, (1283±4) cm⁻¹, (1242±4) cm⁻¹, (1056±4) cm⁻¹ and (823±4) cm⁻¹; or
(1732±4) cm⁻¹, (1587±4) cm⁻¹, (1452±4) cm⁻¹, (1283±4) cm⁻¹, (1242±4) cm⁻¹, (1056±4) cm⁻¹, (1041±4) cm⁻¹ and (823±4) cm⁻¹; or
(1732±4) cm⁻¹, (1587±4) cm⁻¹, (1452±4) cm⁻¹, (1283±4) cm⁻¹, (1242±4) cm⁻¹, (1056±4) cm⁻¹, (1041±4) cm⁻¹, (852±4) cm⁻¹ and (823±4) cm⁻¹; or
(1732±4) cm⁻¹, (1587±4) cm⁻¹, (1452±4) cm⁻¹, (1283±4) cm⁻¹, (1242±4) cm⁻¹, (1056±4) cm⁻¹, (1041±4) cm⁻¹, (852±4) cm⁻¹, (823±4) cm⁻¹ and (381±4) cm⁻¹,
when measured at RT and a wavelength of 785 nm.

In another embodiment, the present invention relates to a co-crystal comprising levothyroxine and L-tartaric acid characterized by having a Raman spectrum comprising peaks at wavenumbers of:
(1242±2) cm⁻¹, (1056±2) cm⁻¹ and (823±2) cm⁻¹; or
(1587±2) cm⁻¹, (1242±2) cm⁻¹, (1056±2) cm⁻¹ and (823±2) cm⁻¹; or
(1732±2) cm⁻¹, (1587±2) cm⁻¹, (1242±2) cm⁻¹, (1056±2) cm⁻¹ and (823±2) cm⁻¹; or
(1732±2) cm⁻¹, (1587±2) cm⁻¹, (1452±2) cm⁻¹, (1242±2) cm⁻¹, (1056±2) cm⁻¹ and (823±2) cm⁻¹; or
(1732±2) cm⁻¹, (1587±2) cm⁻¹, (1452±2) cm⁻¹, (1283±2) cm⁻¹, (1242±2) cm⁻¹, (1056±2) cm⁻¹ and (823±2) cm⁻¹; or
(1732±2) cm⁻¹, (1587±2) cm⁻¹, (1452±2) cm⁻¹, (1283±2) cm⁻¹, (1242±2) cm⁻¹, (1056±2) cm⁻¹, (1041±2) cm⁻¹ and (823±2) cm⁻¹; or
(1732±2) cm⁻¹, (1587±2) cm⁻¹, (1452±2) cm⁻¹, (1283±2) cm⁻¹, (1242±2) cm⁻¹, (1056±2) cm⁻¹, (1041±2) cm⁻¹, (852±2) cm⁻¹ and (823±2) cm⁻¹; or
(1732±2) cm⁻¹, (1587±2) cm⁻¹, (1452±2) cm⁻¹, (1283±2) cm⁻¹, (1242±2) cm⁻¹, (1056±2) cm⁻¹, (1041±2) cm⁻¹, (852±2) cm⁻¹, (823±2) cm⁻¹ and (381±2) cm⁻¹,
when measured at RT and a wavelength of 785 nm.

Figure 3:
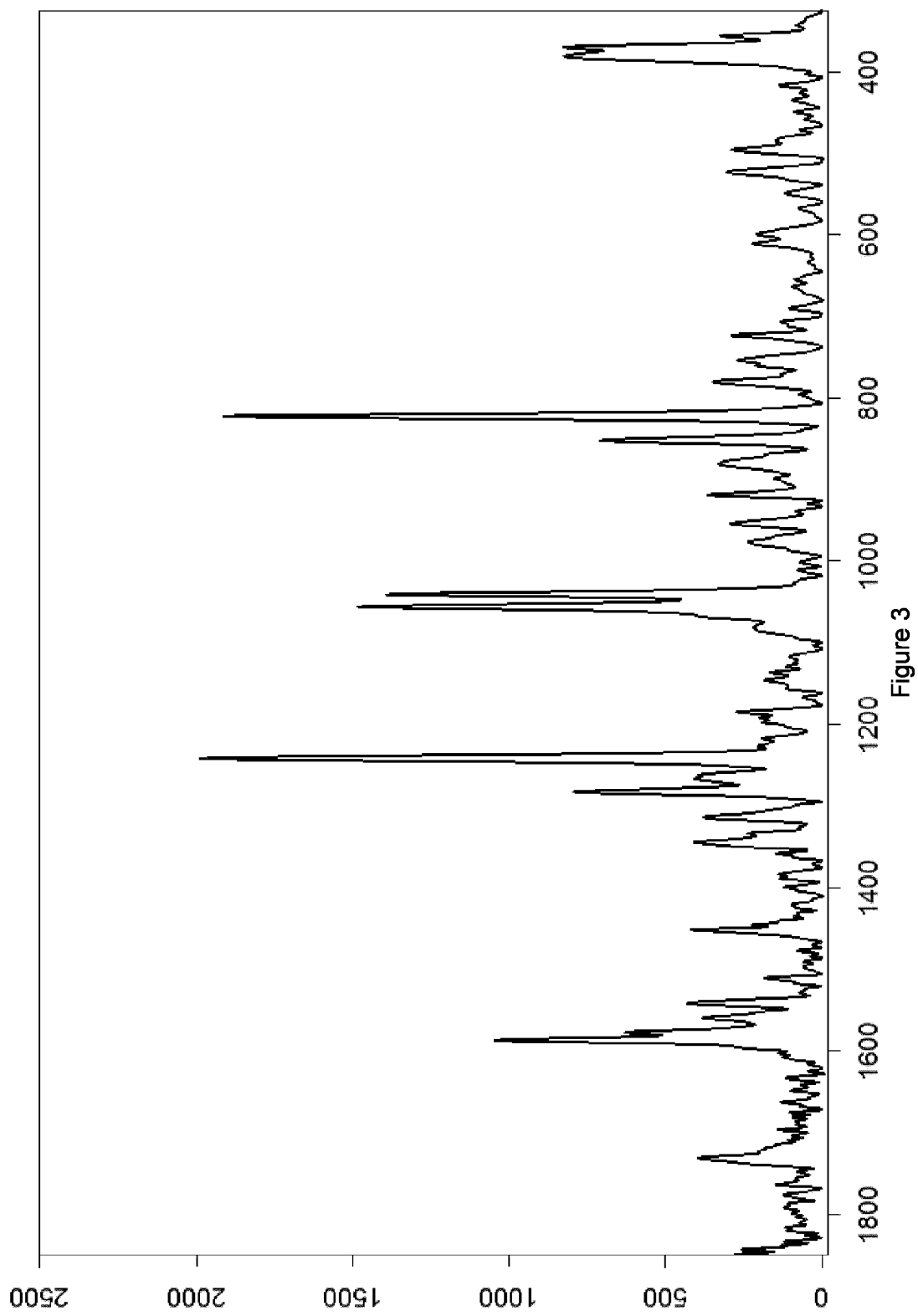
FIG. 3: illustrates a representative Raman spectrum of the co-crystal of the present invention comprising levothyroxine and L-tartaric acid. The x-axis shows the wavenumbers in $cm^{-1}$, the y-axis shows the Raman intensity.

In yet another embodiment, the present invention relates to a co-crystal comprising levothyroxine and L-tartaric acid characterized by having a Raman spectrum essentially the same as shown in FIG. 3 of the present invention, when measured at a temperature in the range of from 20 to 30° C. and a wavelength of 785 nm.

In a further embodiment, the present invention relates to a co-crystal comprising levothyroxine and L-tartaric acid characterized by exhibiting monoclinic unit cells having space group $P2_1\,2_1\,2_1$. Preferably, the unit cells have the following parameters:
a=5.7600(4) Angstrom
b=10.4551(5) Angstrom
c=46.8620(18) Angstrom
alpha=90°
beta=90°
gamma=90°,
when measured with single crystal X-ray diffraction at (173±2) K with Mo-Kalpha$_{1,2}$ radiation having a wavelength of 0.71073 Angstrom.

The present invention also relates to a co-crystal comprising levothyroxine and L-tartaric acid as described in any one of the above defined embodiments characterized in that the co-crystal is an ethanol solvate, preferably an ethanol monosolvate.

Preferably, the invention relates to a co-crystal comprising levothyroxine, L-tartaric acid and ethanol, characterized by having a molar ratio of levothyroxine, L-tartaric acid and ethanol in the range of from 1.0:0.8-1.2:0.8-1.2, preferably of from 1.0:0.9-1.1:0.9-1.1, even more preferably of from 1.00:0.95-1.05:0.95-1.05 and most preferably the molar ratio is 1.0:1.0:1.0.

Alternatively, the invention relates to a co-crystal comprising levothyroxine, L-tartaric acid and ethanol characterized by having a molecular structure as depicted in formula D

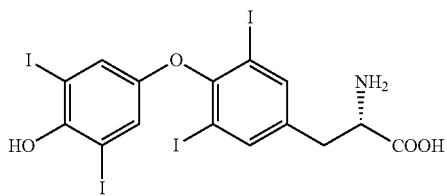
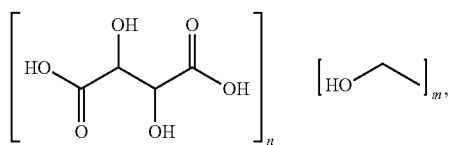

formula D wherein n and m are independently from each other in the range of from 0.8-1.2, preferably from 0.9-1.1, more preferably from 0.95-1.05. Most preferably n and m are 1.0.

In particular, the invention relates to a co-crystal comprising levothyroxine, L-tartaric acid and ethanol characterized by having a molecular structure as depicted in formula E

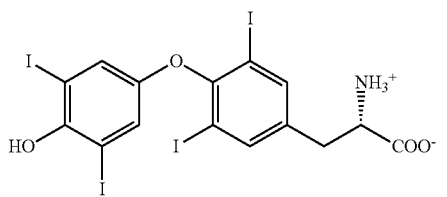
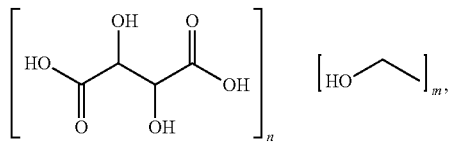

formula E wherein n and m are independently from each other in the range of from 0.8-1.2, preferably from 0.9-1.1, more preferably from 0.95-1.05. Most preferably n and m are 1.0.

In one embodiment, the present invention relates to a co-crystal comprising levothyroxine and L-tartaric acid, characterized by having a DSC curve comprising an endothermic peak, preferably a first endothermic peak, having an onset temperature of (149±5) ° C., preferably of (149±3) ° C., more preferably of (149±1) ° C., when measured with DSC at a heating rate of 15 K/min.

In a further embodiment, the present invention relates to a co-crystal comprising levothyroxine and L-tartaric acid, characterized by having a DSC curve comprising an endothermic peak, preferably a first endothermic peak, having a peak maximum temperature of (165±5) ° C., preferably of (165±3) ° C., more preferably of (165±1) ° C., when measured with DSC at a heating rate of 15 K/min.

In yet another embodiment, the present invention relates to a co-crystal comprising levothyroxine and L-tartaric acid, characterized by having a DSC curve comprising an endothermic peak, preferably a second endothermic peak, having an onset temperature of (180±5) ° C., preferably of (180±3) ° C., more preferably of (180±1) ° C., when measured with DSC at a heating rate of 15 K/min.

In still a further embodiment, the present invention relates to a co-crystal comprising levothyroxine and L-tartaric acid, characterized by having a DSC curve comprising an endothermic peak, preferably a second endothermic peak, having a peak maximum temperature of (197±5) ° C., preferably of (197±3) ° C., more preferably of (197±1) ° C., when measured with DSC at a heating rate of 15 K/min.

In a further aspect, the present invention relates to a process for the preparation of a co-crystal comprising levothyroxine and a dicarboxylic acid, preferably a $C_{2-8}$ dicarboxylic acid, more preferably a $C_{2-6}$ dicarboxylic acid, even more preferably a $C_{2-4}$ dicarboxylic acid and most preferably a $C_4$ dicarboxylic acid in particular L-tartaric acid comprising:

(a) providing a mixture comprising levothyroxine, a dicarboxylic acid, preferably a $C_{2-8}$ dicarboxylic acid, more preferably a $C_{2-6}$ dicarboxylic acid, even more preferably a $C_{2-4}$ dicarboxylic acid and most preferably a $C_4$ dicarboxylic acid, in particular L-tartaric acid and a suitable solvent, wherein the molar ratio of levothyroxine and the dicarboxylic acid, preferably the $C_{2-8}$ dicarboxylic acid, more preferably the $C_{2-6}$ dicarboxylic acid even more preferably the $C_{2-4}$ dicarboxylic acid and most preferably the $C_4$ dicarboxylic acid, in particular L-tartaric acid is in the range of from 1:1.5 to 1:2.5;

(b) stirring the mixture obtained in (a);

(c) separating at least a part of the co-crystals obtained in (b) from the mother liquor;

(d) optionally, washing the isolated co-crystals obtained in (c); and (e) drying the co-crystals obtained step (c) or (d).

Levothyroxine is commercially available (e.g. abcr GmbH). The dicarboxylic acid is preferably a $C_{2-8}$ dicarboxylic acid, more preferably a $C_{2-6}$ dicarboxylic acid even more preferably a $C_{2-4}$ dicarboxylic acid and most preferably a $C_4$ dicarboxylic acid for example selected from the group consisting of adipic acid, aspartic acid (including D-isomer, L-isomer and racemic), fumaric acid, glutamic acid (including D-isomer, L-isomer and racemic), glutaric acid, maleic acid, malic acid (including D-isomer, L-isomer and racemic), malonic acid, oxalic acid, succinic acid and tartaric acid (including D-isomer, L-isomer and racemic). Most preferably, L-tartaric acid is used as co-crystal former in the present process.

In step (a) of the present process an excess of co-crystal fomer is used. The molar ratio of levothyroxine and the dicarboxylic acid, preferably the $C_{2-8}$ dicarboxylic acid, more preferably the $C_{2-6}$ dicarboxylic acid, even more preferably a $C_{2-4}$ dicarboxylic acid and most preferably a $C_4$ dicarboxylic acid in particular L-tartaric acid applied is in the range of from 1.0:1.5-2.5, preferably from 1.0:1.8-2.2, more preferably from 1.0:1.9-2.1 and most preferably the molar ratio is 1.0:2.0.

The suitable solvent, which can be used in step (a) is preferably selected from alcohols e.g. from the group consisting of methanol, ethanol, n-propanol and isopropanol or any mixtures thereof. Most preferably, ethanol is used as solvent in the present process.

The levothyroxine concentration of the mixture provided in step (a) is in the range of from about 30 to 50 g/L, most preferably the levothyroxine concentration is about 40 g/L.

Co-crystallization is accomplished by stirring the mixture provided in step (a). Stirring may be conducted for a period sufficient that at least a substantial part, preferably all of the levothyroxine starting material converts to the desired co-crystal. Preferably stirring is performed at room temperature for a period in the range of from several hours to several days. Stirring may for example be performed for a period in the range of from 2 hours to 7 days e.g. for about 3 days. The skilled person may monitor the conversion of levothyroxine to the desired co-crystal by withdrawing samples from the mixture and analyzing the samples by e.g. powder X-ray diffraction. Stirring may be stopped when certain characteristic reflections of the levothyroxine starting material and the applied co-crystal former are not detectable in the powder X-ray diffractogram anymore.

Once the desired levothyroxine co-crystal is obtained or preferably obtained in essentially pure form, at least a part of the co-crystals is separated from the mother liquor. Preferably, the co-crystals are separated from the mother liquor by any conventional method such as filtration, centrifugation or decantation, more preferably by filtration or centrifugation and most preferably by filtration.

Optionally, in a further step the isolated co-crystals are washed with a suitable solvent. Most preferably, ethanol is used for the optional washing step.

The obtained co-crystals are finally dried. Drying may be performed at a temperature in the range of from about 20 to 80° C., preferably in the range of from about 20 to 40° C. and most preferably drying is performed at RT. Drying may be performed for a period in the range of from about 1 to 72 hours, preferably from about 2 to 48 hours, more preferably from about 4 to 24 hours and most preferably from about 6 to 18 hours. Drying may be performed at ambient pressure and/or under reduced pressure. Preferably, drying is performed at a pressure of about 100 mbar or less, more preferably of about 50 mbar or less and most preferably of about 30 mbar or less, for example a vacuum of about 25 mbar is applied for drying.

Co-Crystal Comprising Levothyroxine, L-Tartaric Acid and L-Lactic Acid

In another embodiment, the invention relates to a co-crystal comprising levothyroxine, L-tartaric acid and L-lactic acid characterized by having a PXRD comprising reflections at 2-Theta angles of:

(3.7±0.2)°, (20.2±0.2)° and (22.4±0.2)°; or (3.7±0.2)°, (13.9±0.2)°, (20.2±0.2)° and (22.4±0.2)°; or (3.7±0.2)°, (13.9±0.2)°, (20.2±0.2)°, (20.7±0.2)° and (22.4±0.2)°; or (3.7±0.2)°, (12.4±0.2)°, (13.9±0.2)°, (20.2±0.2)°, (20.7±0.2)° and (22.4±0.2)°; or (3.7±0.2)°, (12.4±0.2)°, (13.9±0.2)°, (17.7±0.2)°, (20.2±0.2)°, (20.7±0.2)° and (22.4±0.2)°; or (3.7±0.2)°, (12.4±0.2)°, (13.9±0.2)°, (17.7±0.2)°, (20.2±0.2)°, (20.7±0.2)°, (21.0±0.2)° and (22.4±0.2)°; or (3.7±0.2)°, (8.9±0.2)°, (12.4±0.2)°, (13.9±0.2)°, (17.7±0.2)°, (20.2±0.2)°, (20.7±0.2)°, (21.0±0.2)° and (22.4±0.2)°; or (3.7±0.2)°, (8.9±0.2)°, (12.4±0.2)°, (13.9±0.2)°, (17.7±0.2)°, (20.2±0.2)°, (20.7±0.2)°, (21.0±0.2)°, (22.4±0.2)° and (23.0±0.2)°, when measured at RT with Cu-Kalpha$_{1,2}$ radiation having a wavelength of 0.15419 nm.

In yet another embodiment, the invention relates to a co-crystal comprising levothyroxine, L-tartaric acid and L-lactic acid characterized by having a PXRD comprising reflections at 2-Theta angles of (3.7±0.2)°, (17.7±0.2)°, (20.2±0.2)°, (20.7±0.2)°, (21.0±0.2)°, (22.4±0.2)°, (22.7±0.2)°, (23.0±0.2)°, (25.1±0.2)° and (26.0±0.2)°, when measured at RT with Cu-Kalpha$_{1,2}$ radiation having a wavelength of 0.15419 nm.

In a further embodiment, the invention relates to a co-crystal comprising levothyroxine, L-tartaric acid and L-lactic acid characterized by having a PXRD comprising reflections at 2-Theta angles of:

(3.7±0.1)°, (20.2±0.1)° and (22.4±0.1)°; or (3.7±0.1)°, (13.9±0.1)°, (20.2±0.1)° and (22.4±0.1)°; or (3.7±0.1)°, (13.9±0.1)°, (20.2±0.1)°, (20.7±0.1)° and (22.4±0.1)°; or (3.7±0.1)°, (12.4±0.1)°, (13.9±0.1)°, (20.2±0.1)°, (20.7±0.1)° and (22.4±0.1)°; or (3.7±0.1)°, (12.4±0.1)°, (13.9±0.1)°, (17.7±0.1)°, (20.2±0.1)°, (20.7±0.1)° and (22.4±0.1)°; or (3.7±0.1)°, (12.4±0.1)°, (13.9±0.1)°, (17.7±0.1)°, (20.2±0.1)°, (20.7±0.1)°, (21.0±0.1)° and (22.4±0.1)°; or (3.7±0.1)°, (8.9±0.1)°, (12.4±0.1)°, (13.9±0.1)°, (17.7±0.1)°, (20.2±0.1)°, (20.7±0.1)°, (21.0±0.1)° and (22.4±0.1)°; or (3.7±0.1)°, (8.9±0.1)°, (12.4±0.1)°, (13.9±0.1)°, (17.7±0.1)°, (20.2±0.1)°, (20.7±0.1)°, (21.0±0.1)°, (22.4±0.1)° and (23.0±0.1)°, when measured at RT with Cu-Kalpha$_{1,2}$ radiation having a wavelength of 0.15419 nm.

In yet another embodiment, the invention relates to a co-crystal comprising levothyroxine, L-tartaric acid and L-lactic acid characterized by having a PXRD comprising reflections at 2-Theta angles of (3.7±0.1)°, (17.7±0.1)°, (20.2±0.1)°, (20.7±0.1)°, (21.0±0.1)°, (22.4±0.1)°, (22.7±0.1)°, (23.0±0.1)°, (25.1±0.1)° and (26.0±0.1)°, when measured at RT with Cu-Kalpha$_{1,2}$ radiation having a wavelength of 0.15419 nm.

Figure 9:
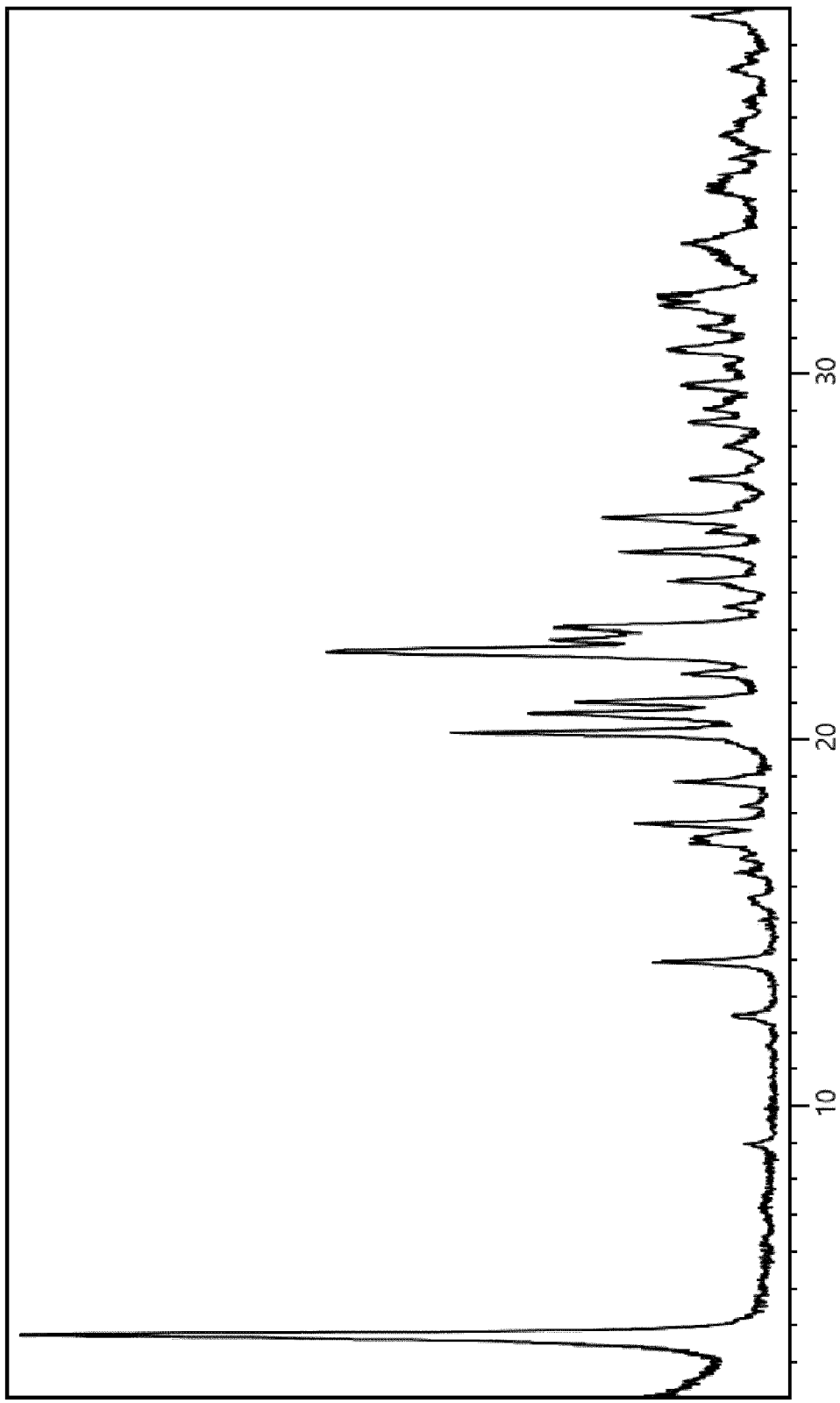
FIG. 9: illustrates a representative PXRD of the co-crystal of the present invention comprising levothyroxine, L-tartaric acid and L-lactic acid. The x-axis shows the scattering angle in ° 2-Theta, the y-axis shows the relative intensity of the scattered X-ray beam in counts of detected photons.

In still another embodiment, the present invention relates to a co-crystal comprising levothyroxine, L-tartaric acid and L-lactic acid characterized by having a PXRD essentially the same as shown in FIG. 9 of the present invention, when measured at RT with Cu-Kalpha$_{1,2}$ radiation having a wavelength of 0.15419 nm.

In one embodiment, the present invention relates to a co-crystal comprising levothyroxine, L-tartaric acid and L-lactic acid characterized by having an FTIR spectrum comprising peaks at wavenumbers of:

(1440±4) cm$^{-1}$, (1238±4) cm$^{-1}$ and (1084±4) cm$^{-1}$ or;

(3456±4) cm$^{-1}$, (1440±4) cm$^{-1}$, (1238±4) cm$^{-1}$ and (1084±4) cm$^{-1}$; or (3456±4) cm$^{-1}$, (1768±4) cm$^{-1}$, (1440±4) cm$^{-1}$, (1238±4) cm$^{-1}$ and (1084±4) cm$^{-1}$; or (3456±4) cm$^{-1}$, (1768±4) cm$^{-1}$, (1722±4) cm$^{-1}$, (1440±4) cm$^{-1}$, (1238±4) cm$^{-1}$ and (1084±4) cm$^{-1}$; or (3456±4) cm$^{-1}$, (1768±4) cm$^{-1}$, (1722±4) cm$^{-1}$, (1588±4) cm$^{-1}$, (1440±4) cm$^{-1}$, (1238±4) cm$^{-1}$ and (1084±4) cm$^{-1}$; or (3456±4) cm$^{-1}$, (1768±4) cm$^{-1}$, (1722±4) cm$^{-1}$, (1588±4) cm$^{-1}$, (1440±4) cm$^{-1}$, (1238±4) cm$^{-1}$, (1084±4) cm$^{-1}$ and (992±4) cm$^{-1}$; or (3456±4) cm$^{-1}$, (1768±4) cm$^{-1}$, (1722±4) cm$^{-1}$, (1588±4) cm$^{-1}$, (1440±4) cm$^{-1}$, (1238±4) cm$^{-1}$, (1084±4) cm$^{-1}$, (992±4) cm$^{-1}$ and (753±4) cm$^{-1}$; or (3456±4) cm$^{-1}$, (1768±4) cm$^{-1}$, (1722±4) cm$^{-1}$, (1588±4) cm$^{-1}$, (1440±4) cm$^{-1}$, (1238±4) cm$^{-1}$, (1084±4) cm$^{-1}$, (992±4) cm$^{-1}$, (753±4) cm$^{-1}$ and (661±4) cm$^{-1}$, when measured at RT with a diamond ATR cell.

In another embodiment, the present invention relates to a co-crystal comprising levothyroxine, L-tartaric acid and L-lactic acid characterized by having an FTIR spectrum comprising peaks at wavenumbers of:
(1440±2) cm$^{-1}$, (1238±2) cm$^{-1}$ and (1084±2) cm$^{-1}$ or;
(3456±2) cm$^{-1}$, (1440±2) cm$^{-1}$, (1238±2) cm$^{-1}$ and (1084±2) cm$^{-1}$; or

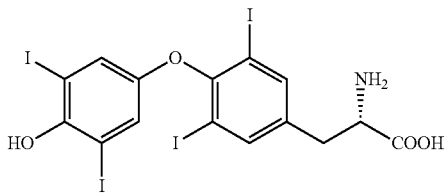

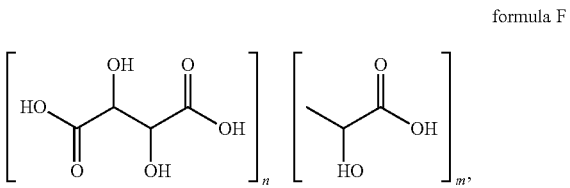

(3456±2) cm$^{-1}$, (1768±2) cm$^{-1}$, (1440±2) cm$^{-1}$, (1238±2) cm$^{-1}$ and (1084±2) cm$^{-1}$; or (3456±2) cm$^{-1}$, (1768±2) cm$^{-1}$, (1722±2) cm$^{-1}$, (1440±2) cm$^{-1}$, (1238±2) cm$^{-1}$ and (1084±2) cm$^{-1}$; or (3456±2) cm$^{-1}$, (1768±2) cm$^{-1}$, (1722±2) cm$^{-1}$, (1588±2) cm$^{-1}$, (1440±2) cm$^{-1}$, (1238±4) cm$^{-1}$ and (1084±2) cm$^{-1}$; or (3456±2) cm$^{-1}$, (1768±2) cm$^{-1}$, (1722±2) cm$^{-1}$, (1588±2) cm$^{-1}$, (1440±2) cm$^{-1}$, (1238±2) cm$^{-1}$, (1084±2) cm$^{-1}$ and (992±2) cm$^{-1}$; or (3456±2) cm$^{-1}$, (1768±2) cm$^{-1}$, (1722±2) cm$^{-1}$, (1588±2) cm$^{-1}$, (1440±2) cm$^{-1}$, (1238±2) cm$^{-1}$, (1084±2) cm$^{-1}$, (992±2) cm$^{-1}$ and (753±2) cm$^{-1}$; or (3456±2) cm$^{-1}$, (1768±2) cm$^{-1}$, (1722±2) cm$^{-1}$, (1588±2) cm$^{-1}$, (1440±2) cm$^{-1}$, (1238±2) cm$^{-1}$, (1084±2) cm$^{-1}$, (992±2) cm$^{-1}$, (753±2) cm$^{-1}$ and (661±2) cm$^{-1}$, when measured at RT with a diamond ATR cell.

Figure 10:
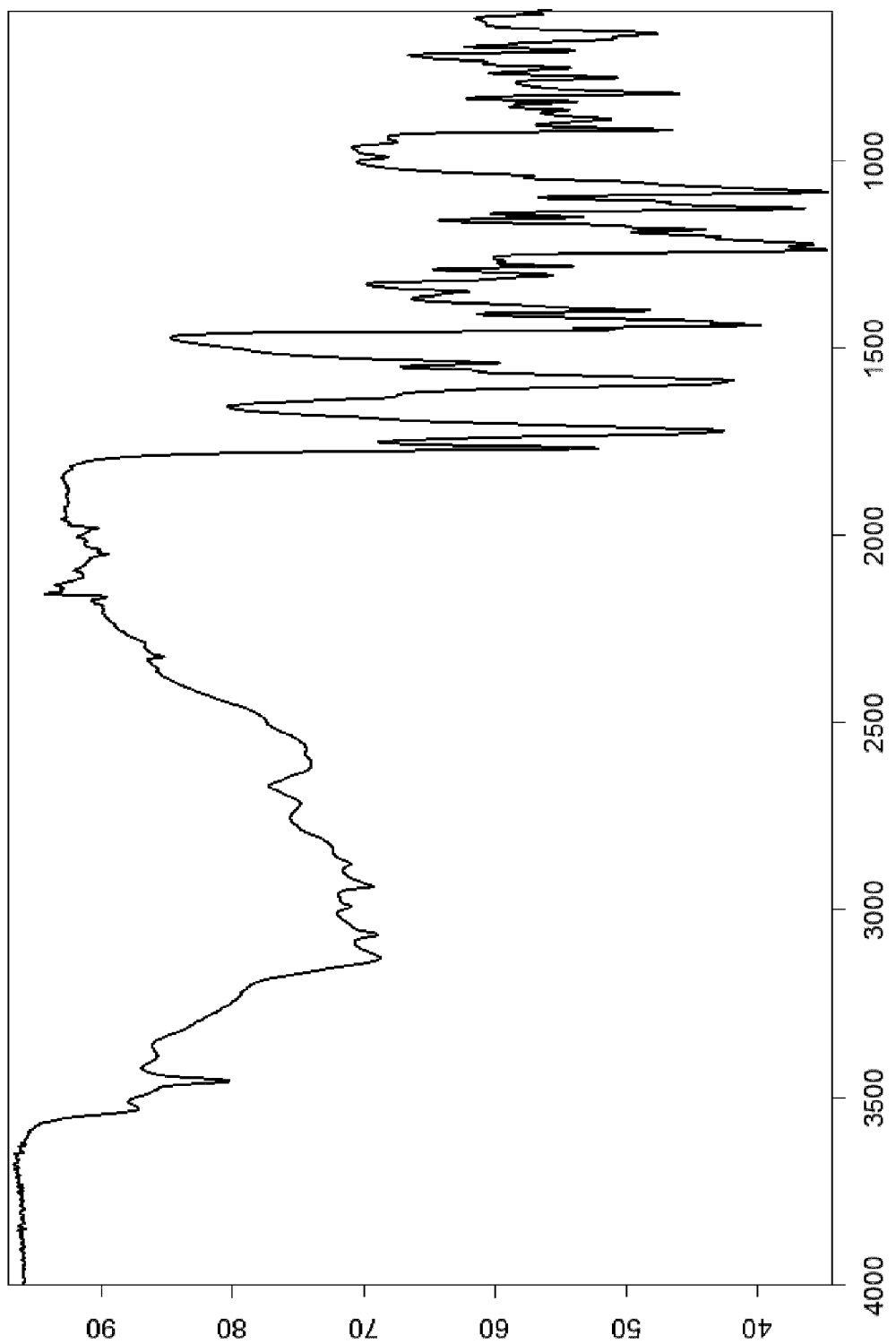
FIG. 10: illustrates a representative FTIR spectrum of the co-crystal of the present invention comprising levothyroxine, L-tartaric acid and L-lactic acid. The x-axis shows the wavenumbers in $cm^{-1}$, the y-axis shows the relative intensity in percent transmittance.

In yet another embodiment, the present invention relates to a co-crystal comprising levothyroxine, L-tartaric acid and L-lactic acid characterized by having an FTIR spectrum essentially the same as shown in FIG. 10 of the present invention, when measured at RT with a diamond ATR cell.

Preferably, the invention relates to a co-crystal comprising levothyroxine, L-tartaric acid and L-lactic acid, characterized by having a molar ratio of levothyroxine, L-tartaric acid and L-lactic acid in the range of from 1.0:0.8-1.2:0.8-1.2, preferably of from 1.0:0.9-1.1:0.9-1.1, even more preferably of from 1.00:0.95-1.05:0.95-1.05 and most preferably the molar ratio is 1.0:1.0:1.0.

Alternatively, the invention relates to a co-crystal comprising levothyroxine, L-tartaric acid and L-lactic acid characterized by having a molecular structure as depicted in formula F formula F

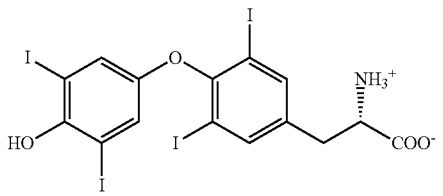

wherein n and m are independently from each other in the range of from 0.8-1.2, preferably from 0.9-1.1, more preferably from 0.95-1.05. Most preferably n and m are 1.0.

In particular, the invention relates to a co-crystal comprising levothyroxine, L-tartaric acid and L-lactic acid characterized by having a molecular structure as depicted in formula G formula G

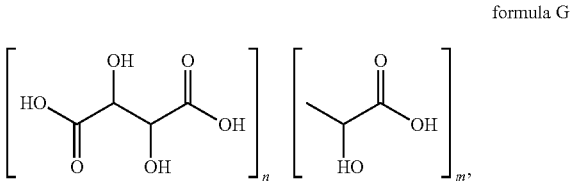

wherein n and m are independently from each other in the range of from 0.8-1.2, preferably from 0.9-1.1, more preferably from 0.95-1.05. Most preferably n and m are 1.0.

In one embodiment, the present invention relates to a co-crystal comprising levothyroxine, L-tartaric acid and L-lactic acid characterized by having a DSC curve comprising an endothermic peak, preferably a first endothermic peak, having an onset temperature of (151±5) ° C., preferably of (151±3) ° C., more preferably of (151±1) ° C., when measured with DSC at a heating rate of 20 K/min.

In a further embodiment, the present invention relates to a co-crystal comprising levothyroxine, L-tartaric acid and L-lactic acid characterized by having a DSC curve comprising an endothermic peak, preferably a first endothermic peak, having a peak maximum at a temperature of (162±5) ° C., preferably of (162±3) ° C., more preferably of (162±1) ° C., when measured with DSC at a heating rate of 20 K/min.

In a further aspect, the present invention relates to a process for the preparation of the co-crystal comprising levothyroxine, L-tartaric acid and L-lactic acid as defined in any one of the above described embodiments comprising:
(a) providing a mixture comprising levothyroxine, L-tartaric acid, L-lactic acid and a suitable solvent, wherein the molar ratio of levothyroxine, L-tartaric acid and L-lactic acid is in the range of from about 1.0:2.0:8.0;
(b) stirring the mixture obtained in (a);
(c) separating at least a part of the crystals obtained in (b) from the mother liquor;
(d) optionally, washing the isolated crystals obtained in (c); and
(e) drying the crystals obtained step (c) or (d).

Commercially available levothyroxine (e.g. from abcr GmbH) is treated in step (a) with an excess of the co-crystal formers L-tartaric acid and L-lactic acid. The molar ratio of levothyroxine, L-tartaric acid and L-lactic acid applied is thereby in the range of from about 1.0:2.0:8.0.

The suitable solvent, which can be used in step (a) is preferably selected from ethers e.g. from the group consisting of methyl acetate, ethyl acetate, n-propyl acetate, isopropyl acetate and isobutyl acetate or any mixtures thereof. Most preferably, isobutyl acetate is used as solvent in the present process.

The levothyroxine concentration of the mixture provided in step (a) is in the range of from about 80 to 120 g/L, most preferably the levothyroxine concentration is about 100 g/L solvent or solvent mixture.

Co-crystallization is accomplished by stirring the mixture provided in step (a). Stirring may be performed at room temperature. More preferably, stirring may be performed at a temperature in the range of from about 10° C. to 20° C. In a particular preferred embodiment, stirring may be performed by varying the temperature between a range of from 10° C. to 20° C. Stirring may be conducted for a period sufficient that at least a substantial part, preferably all of the levothyroxine starting material converts to the levothyroxine L-tartaric acid L-lactic acid co-crystal. Thereby, the stirring period may range from several hours to several days, for example stirring may be conducted for a period in the range of from about 2 hours to 10 days e.g. for about 7 days. The skilled person may monitor the conversion of levothyroxine to the levothyroxine L-tartaric acid L-lactic acid co-crystal by withdrawing samples from the mixture and analyzing the samples by e.g. powder X-ray diffraction. Stirring may be stopped when certain characteristic reflections of the levothyroxine starting material and the applied co-crystal formers are not detectable in the powder X-ray diffractogram anymore.

Once the desired levothyroxine L-tartaric acid L-lactic acid co-crystal is obtained or preferably obtained in essentially pure form, at least a part of the crystals is separated from the mother liquor. Preferably, the crystals are separated from the mother liquor by any conventional method such as filtration, centrifugation or decantation, more preferably by filtration or centrifugation and most preferably by filtration.

Optionally, in a further step the isolated crystals are washed with a suitable solvent, e.g. one or more ethers selected from the group consisting of methyl acetate, ethyl acetate, n-propyl acetate, isopropyl acetate and isobutyl acetate. Most preferably, isobutyl acetate is used for the optional washing step.

The obtained crystals are finally dried. Drying may be performed at a temperature in the range of from about 20 to 80° C., preferably in the range of from about 20 to 40° C. and most preferably drying is performed at RT. Drying may be performed for a period in the range of from about 1 to 72 hours, preferably from about 2 to 48 hours, more preferably from about 4 to 24 hours and most preferably from about 6 to 18 hours. Drying may be performed at ambient pressure and/or under reduced pressure. Preferably, drying is performed at a pressure of about 100 mbar or less, more preferably of about 50 mbar or less and most preferably of about 30 mbar or less, for example a vacuum of about 25 mbar is applied for drying.

Co-Crystal Comprising Levothyroxine and Oxalic Acid

In another embodiment, the invention relates to a co-crystal comprising levothyroxine and oxalic acid characterized by having a PXRD comprising reflections at 2-Theta angles of:
$(3.6\pm0.2)°$, $(13.7\pm0.2)°$ and $(22.2\pm0.2)°$; or
$(3.6\pm0.2)°$, $(13.7\pm0.2)°$, $(16.7\pm0.2)°$ and $(22.2\pm0.2)°$; or
$(3.6\pm0.2)°$, $(13.7\pm0.2)°$, $(16.7\pm0.2)°$, $(20.5\pm0.2)°$ and $(22.2\pm0.2)°$; or
$(3.6\pm0.2)°$, $(13.7\pm0.2)°$, $(16.7\pm0.2)°$, $(19.9\pm0.2)°$, $(20.5\pm0.2)°$ and $(22.2\pm0.2)°$; or
$(3.6\pm0.2)°$, $(9.2\pm0.2)°$, $(13.7\pm0.2)°$, $(16.7\pm0.2)°$, $(19.9\pm0.2)°$, $(20.5\pm0.2)°$ and $(22.2\pm0.2)°$; or
$(3.6\pm0.2)°$, $(9.2\pm0.2)°$, $(13.7\pm0.2)°$, $(16.7\pm0.2)°$, $(18.2\pm0.2)°$, $(19.9\pm0.2)°$, $(20.5\pm0.2)°$ and $(22.2\pm0.2)°$; or
$(3.6\pm0.2)°$, $(9.2\pm0.2)°$, $(13.7\pm0.2)°$, $(16.7\pm0.2)°$, $(18.2\pm0.2)°$, $(19.9\pm0.2)°$, $(20.5\pm0.2)°$, $(22.2\pm0.2)°$ and $(22.7\pm0.2)°$; or
$(3.6\pm0.2)°$, $(9.2\pm0.2)°$, $(13.7\pm0.2)°$, $(16.7\pm0.2)°$, $(18.2\pm0.2)°$, $(19.9\pm0.2)°$, $(20.5\pm0.2)°$, $(22.2\pm0.2)°$, $(22.7\pm0.2)°$ and $(23.5\pm0.2)°$,
when measured at RT with Cu-Kalpha$_{1,2}$ radiation having a wavelength of 0.15419 nm.

In a further embodiment, the invention relates to a co-crystal comprising levothyroxine and oxalic acid characterized by having a PXRD comprising reflections at 2-Theta angles of:
$(3.6\pm0.1)°$, $(13.7\pm0.1)°$ and $(22.2\pm0.1)°$; or
$(3.6\pm0.1)°$, $(13.7\pm0.1)°$, $(16.7\pm0.1)°$ and $(22.2\pm0.1)°$; or
$(3.6\pm0.1)°$, $(13.7\pm0.1)°$, $(16.7\pm0.1)°$, $(20.5\pm0.1)°$ and $(22.2\pm0.1)°$; or
$(3.6\pm0.1)°$, $(13.7\pm0.1)°$, $(16.7\pm0.1)°$, $(19.9\pm0.1)°$, $(20.5\pm0.1)°$ and $(22.2\pm0.1)°$; or
$(3.6\pm0.1)°$, $(9.2\pm0.1)°$, $(13.7\pm0.1)°$, $(16.7\pm0.1)°$, $(19.9\pm0.1)°$, $(20.5\pm0.1)°$ and $(22.2\pm0.1)°$; or
$(3.6\pm0.1)°$, $(9.2\pm0.1)°$, $(13.7\pm0.2)°$, $(16.7\pm0.2)°$, $(18.2\pm0.2)°$, $(19.9\pm0.2)°$, $(20.5\pm0.2)°$ and $(22.2\pm0.2)°$; or
$(3.6\pm0.1)°$, $(9.2\pm0.1)°$, $(13.7\pm0.1)°$, $(16.7\pm0.1)°$, $(18.2\pm0.1)°$, $(19.9\pm0.1)°$, $(20.5\pm0.1)°$, $(22.2\pm0.1)°$ and $(22.7\pm0.1)°$; or
$(3.6\pm0.1)°$, $(9.2\pm0.1)°$, $(13.7\pm0.1)°$, $(16.7\pm0.1)°$, $(18.2\pm0.1)°$, $(19.9\pm0.1)°$, $(20.5\pm0.1)°$, $(22.2\pm0.1)°$, $(22.7\pm0.1)°$ and $(23.5\pm0.1)°$,
when measured at RT with Cu-Kalpha$_{1,2}$ radiation having a wavelength of 0.15419 nm.

Figure 12:
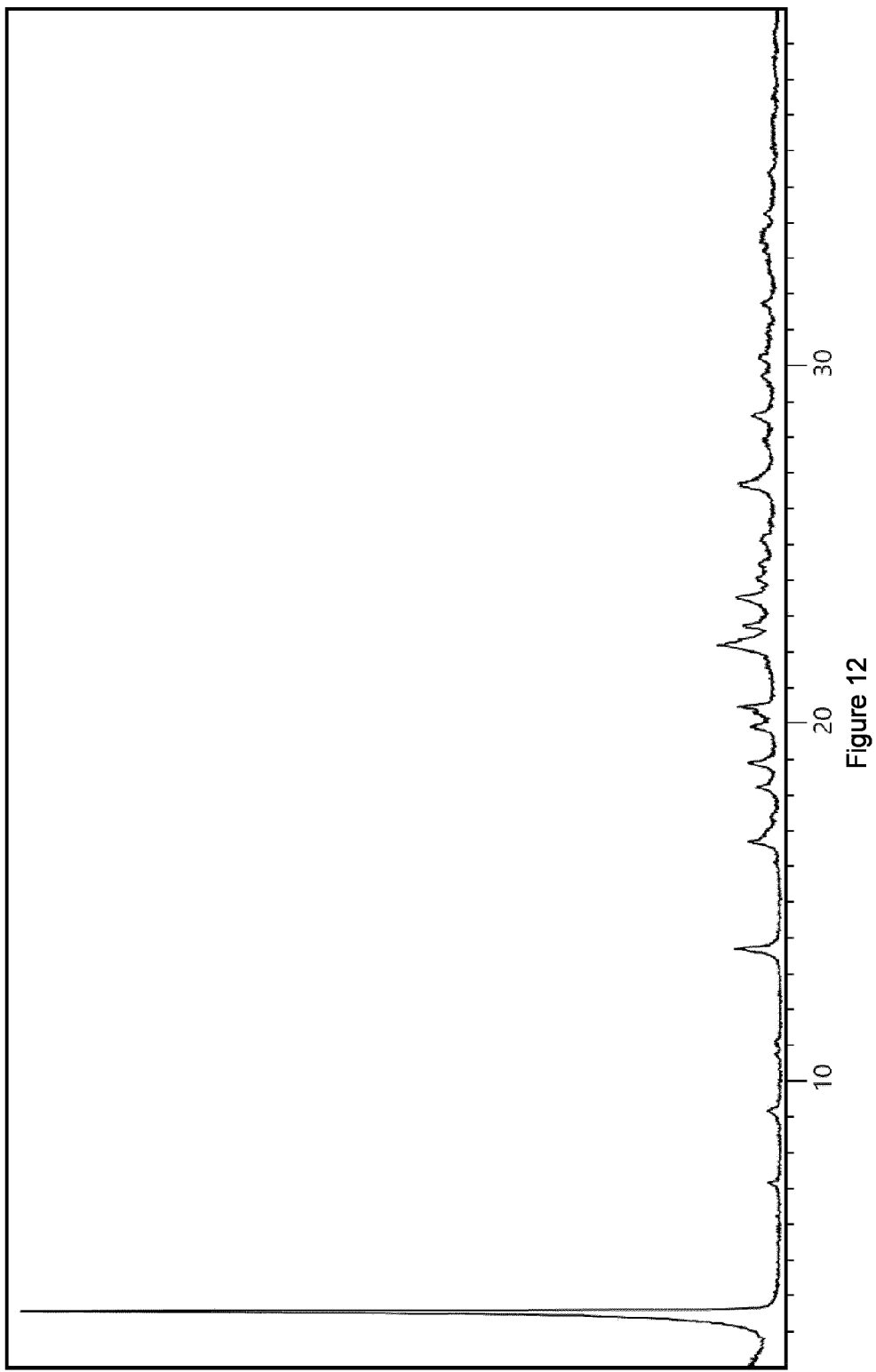
FIG. 12: illustrates a representative PXRD of the co-crystal of the present invention comprising levothyroxine and oxalic acid. The x-axis shows the scattering angle in ° 2-Theta, the y-axis shows the relative intensity of the scattered X-ray beam in counts of detected photons.

In still another embodiment, the present invention relates to a co-crystal comprising levothyroxine and oxalic acid characterized by having a PXRD essentially the same as shown in FIG. 12 of the present invention, when measured at RT with Cu-Kalpha$_{1,2}$ radiation having a wavelength of 0.15419 nm.

In one embodiment, the present invention relates to a co-crystal comprising levothyroxine and oxalic acid characterized by having an FTIR spectrum comprising peaks at wavenumbers of:
$(1631\pm4)$ cm$^{-1}$, $(1432\pm4)$ cm$^{-1}$ and $(708\pm4)$ cm$^{-1}$ or;
$(1631\pm4)$ cm$^{-1}$, $(1518\pm4)$ cm$^{-1}$, $(1432\pm4)$ cm$^{-1}$ and $(708\pm4)$ cm$^{-1}$; or (3466±4) cm⁻¹, (1631±4) cm⁻¹, (1518±4) cm⁻¹, (1432±4) cm⁻¹ and (708±4) cm⁻¹; or
(3466±4) cm⁻¹, (1726±4) cm⁻¹, (1631±4) cm⁻¹, (1518±4) cm⁻¹, (1432±4) cm⁻¹ and (708±4) cm⁻¹; or
(3466±4) cm⁻¹, (1726±4) cm⁻¹, (1631±4) cm⁻¹, (1585±4) cm⁻¹, (1518±4) cm⁻¹, (1432±4) cm⁻¹ and (708±4) cm⁻¹; or
(3466±4) cm⁻¹, (1726±4) cm⁻¹, (1631±4) cm⁻¹, (1585±4) cm⁻¹, (1518±4) cm⁻¹, (1432±4) cm⁻¹, (1150±4) cm⁻¹ and (708±4) cm⁻¹; or
(3466±4) cm⁻¹, (1726±4) cm⁻¹, (1631±4) cm⁻¹, (1585±4) cm⁻¹, (1518±4) cm⁻¹, (1432±4) cm⁻¹, (1150±4) cm⁻¹, (1039±4) cm⁻¹ and (708±4) cm⁻¹; or
(3466±4) cm⁻¹, (1726±4) cm⁻¹, (1631±4) cm⁻¹, (1585±4) cm⁻¹, (1518±4) cm⁻¹, (1432±4) cm⁻¹, (1150±4) cm⁻¹, (1039±4) cm⁻¹, (797±4) cm⁻¹ and (708±4) cm⁻¹,
when measured at RT with a diamond ATR cell.

In another embodiment, the present invention relates to a co-crystal comprising levothyroxine and oxalic acid characterized by having an FTIR spectrum comprising peaks at wavenumbers of:
(1631±2) cm⁻¹, (1432±2) cm⁻¹ and (708±2) cm⁻¹ or;
(1631±2) cm⁻¹, (1518±2) cm⁻¹, (1432±2) cm⁻¹ and (708±2) cm⁻¹; or
(3466±2) cm⁻¹, (1631±2) cm⁻¹, (1518±2) cm⁻¹, (1432±2) cm⁻¹ and (708±2) cm⁻¹; or
(3466±2) cm⁻¹, (1726±2) cm⁻¹, (1631±2) cm⁻¹, (1518±2) cm⁻¹, (1432±2) cm⁻¹ and (708±2) cm⁻¹; or
(3466±2) cm⁻¹, (1726±2) cm⁻¹, (1631±2) cm⁻¹, (1585±2) cm⁻¹, (1518±2) cm⁻¹, (1432±2) cm⁻¹ and (708±2) cm⁻¹; or
(3466±2) cm⁻¹, (1726±2) cm⁻¹, (1631±2) cm⁻¹, (1585±2) cm⁻¹, (1518±2) cm⁻¹, (1432±2) cm⁻¹, (1150±2) cm⁻¹ and (708±2) cm⁻¹; or
(3466±2) cm⁻¹, (1726±2) cm⁻¹, (1631±2) cm⁻¹, (1585±2) cm⁻¹, (1518±2) cm⁻¹, (1432±2) cm⁻¹, (1150±2) cm⁻¹, (1039±2) cm⁻¹ and (708±2) cm⁻¹; or
(3466±2) cm⁻¹, (1726±2) cm⁻¹, (1631±2) cm⁻¹, (1585±2) cm⁻¹, (1518±2) cm⁻¹, (1432±2) cm⁻¹, (1150±2) cm⁻¹, (1039±2) cm⁻¹, (797±2) cm⁻¹ and (708±2) cm⁻¹,
when measured at RT with a diamond ATR cell.

Figure 13:
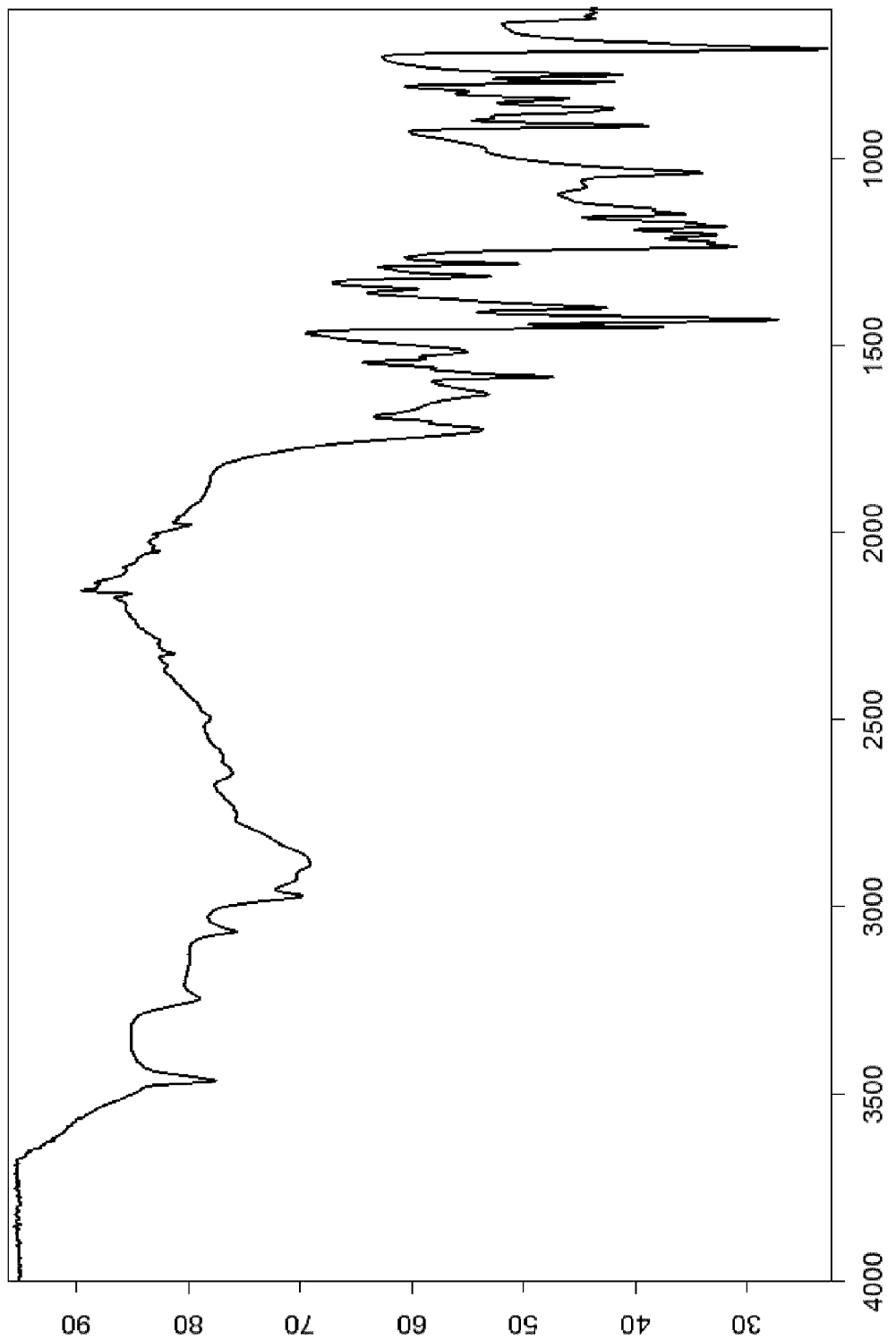
FIG. 13: illustrates a representative FTIR spectrum of the co-crystal of the present invention comprising levothyroxine and oxalic acid. The x-axis shows the wavenumbers in $cm^{-1}$, the y-axis shows the relative intensity in percent transmittance.

In yet another embodiment, the present invention relates to a co-crystal comprising levothyroxine and oxalic acid characterized by having an FTIR spectrum essentially the same as shown in FIG. 13 of the present invention, when measured at RT with a diamond ATR cell.

The present invention also relates to a co-crystal comprising levothyroxine and oxalic acid as described in any one of the above defined embodiments characterized in that the co-crystal is an ethanol solvate, preferably an ethanol mono solvate.

Preferably, the invention relates to a co-crystal comprising levothyroxine, oxalic acid and ethanol, characterized by having a molar ratio of levothyroxine, oxalic acid and ethanol in the range of from 1.0:0.8-1.2:0.8-1.2, preferably of from 1.0:0.9-1.1:0.9-1.1, even more preferably of from 1.00:0.95-1.05:0.95-1.05 and most preferably the molar ratio is 1.0:1.0:1.0. In another embodiment, the co-crystal comprising levothyroxine, oxalic acid and ethanol may be characterized by having a molar ratio of levothyroxine, oxalic acid and ethanol in the range of from 1.0:1.8-2.2:0.8-1.2, preferably of from 1.0:1.9-2.1:0.9-1.1, even more preferably of from 1.00:1.95-2.05:0.95-1.05 and most preferably the molar ratio is 1.0:2.0:1.0.

Alternatively, the invention relates to a co-crystal comprising levothyroxine, oxalic acid and ethanol characterized by having a molecular structure as depicted in formula H formula H

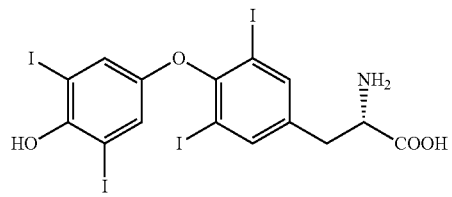 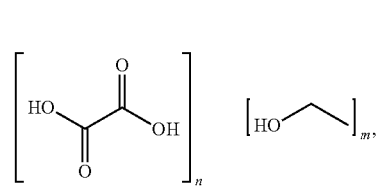

wherein n and m are independently from each other in the range of from 0.8-1.2, preferably from 0.9-1.1, more preferably from 0.95-1.05. Most preferably n and m are 1.0.

In another embodiment, n is in the range of from 1.8-2.2, preferably from 1.9-2.1, more preferably from 1.95-2.05 and most preferably n is 2.0, while m is in the range of from 0.8-1.2, preferably from 0.9-1.1, more preferably from 0.95-1.05 and most preferably m is 1.0.

In particular, the invention relates to a co-crystal comprising levothyroxine, oxalic acid and ethanol characterized by having a molecular structure as depicted in formula I formula I

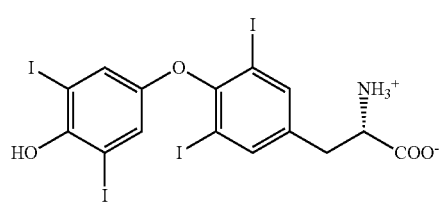 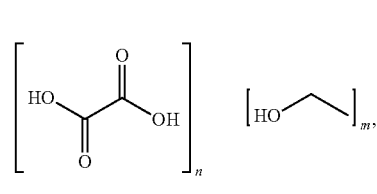

wherein n and m are independently from each other in the range of from 0.8-1.2, preferably from 0.9-1.1, more preferably from 0.95-1.05. Most preferably n and m are 1.0.

In another embodiment, n is in the range of from 1.8-2.2, preferably from 1.9-2.1, more preferably from 1.95-2.05 and most preferably n is 2.0, while m is in the range of from 0.8-1.2, preferably from 0.9-1.1, more preferably from 0.95-1.05 and most preferably m is 1.0.

In a further aspect, the present invention relates to a process for the preparation of the co-crystal comprising levothyroxine and oxalic acid as defined in any one of the above described embodiments comprising:

(a) providing a mixture comprising levothyroxine, oxalic acid and a suitable solvent, wherein the molar ratio of levothyroxine and oxalic acid is in the range of from about 1.0:2.0;

(b) stirring the mixture obtained in (a);

(c) separating at least a part of the crystals obtained in (b) from the mother liquor;

(d) optionally, washing the isolated crystals obtained in (c); and (e) drying the crystals obtained step (c) or (d).

Commercially available levothyroxine (e.g. from abcr GmbH) is treated in step (a) with an excess of the co-crystal former oxalic acid. The molar ratio of levothyroxine and oxalic acid applied is thereby in the range of from about 1.0:2.0.

The suitable solvent, which can be used in step (a) is preferably selected from alcohols e.g. from the group consisting of methanol, ethanol, n-propanol and isopropanol or any mixtures thereof. Most preferably, ethanol is used as solvent in the present process.

The levothyroxine concentration of the mixture provided in step (a) is in the range of from about 80 to 120 g/L, most preferably the levothyroxine concentration is about 100 g/L solvent or solvent mixture.

Co-crystallization is accomplished by stirring the mixture provided in step (a). Stirring may be performed at room temperature. More preferably, stirring may be performed at a temperature in the range of from about 10° C. to 20° C. In a particular preferred embodiment, stirring may be performed by varying the temperature between a range of from 10° C. to 20° C. Stirring may be conducted for a period sufficient that at least a substantial part, preferably all of the levothyroxine starting material converts to the levothyroxine oxalic acid co-crystal. Thereby, the stirring period may range from several hours to several days, for example stirring may be conducted for a period in the range of from about 2 hours to 10 days e.g. for about 5 days. The skilled person may monitor the conversion of levothyroxine to the levothyroxine oxalic acid co-crystal by withdrawing samples from the mixture and analyzing the samples by e.g. powder X-ray diffraction. Stirring may be stopped when certain characteristic reflections of the levothyroxine starting material and the applied co-crystal formers are not detectable in the powder X-ray diffractogram anymore.

Once the desired levothyroxine oxalic acid co-crystal is obtained or preferably obtained in essentially pure form, at least a part of the crystals is separated from the mother liquor. Preferably, the crystals are separated from the mother liquor by any conventional method such as filtration, centrifugation or decantation, more preferably by filtration or centrifugation and most preferably by filtration.

Optionally, in a further step the isolated crystals are washed with a suitable solvent, which may be selected from alcohols e.g. from the group consisting of methanol, ethanol, n-propanol and isopropanol or any mixtures thereof. Most preferably, ethanol is used for the optional washing step.

The obtained crystals are finally dried. Drying may be performed at a temperature in the range of from about 20 to 40° C., preferably drying is performed at RT. Drying may be performed for a period in the range of from about 1 to 72 hours, preferably from about 2 to 48 hours, more preferably from about 4 to 24 hours and most preferably from about 6 to 18 hours. Drying may be performed at ambient pressure and/or under reduced pressure. Preferably, drying is performed at a pressure of about 100 mbar or less, more preferably of about 50 mbar or less and most preferably of about 30 mbar or less, for example a vacuum of about 25 mbar is applied for drying.

Pharmaceutical Compositions and Medical Use

In a further aspect, the present invention relates to the use of a co-crystal comprising levothyroxine and a dicarboxylic acid, preferably a $C_{2-8}$ dicarboxylic acid, more preferably a $C_{2-6}$ dicarboxylic acid, even more preferably a $C_{2-4}$ dicarboxylic acid and most preferably a $C_4$ dicarboxylic acid, in particular L-tartaric acid or oxalic acid for the preparation of a pharmaceutical composition.

In a further aspect, the present invention relates to a pharmaceutical composition containing a co-crystal comprising levothyroxine and a dicarboxylic acid, preferably a $C_{2-8}$ dicarboxylic acid, more preferably a $C_{2-6}$ dicarboxylic acid, even more preferably a $C_{2-4}$ dicarboxylic acid and most preferably a $C_4$ dicarboxylic acid, in particular L-tartaric acid or oxalic acid, preferably in a predetermined and/or effective amount, and at least one pharmaceutically acceptable excipient.

Preferably, the predetermined and/or effective amount of the co-crystal comprising levothyroxine and a dicarboxylic acid, preferably a $C_{2-8}$ dicarboxylic acid, more preferably a $C_{2-6}$ dicarboxylic acid, even more preferably a $C_{2-4}$ dicarboxylic acid and most preferably a $C_4$ dicarboxylic acid, in particular L-tartaric acid or oxalic acid is selected such, that the final levothyroxine co-crystal dose is equivalent to a levothyroxine sodium dose of 25 to 300 microgramm calculated as anhydrous levothyroxine sodium. For example the predetermined and/or effective amount of the co-crystal comprising levothyroxine and a dicarboxylic acid, preferably a $C_{2-8}$ dicarboxylic acid, more preferably a $C_{2-6}$ dicarboxylic acid, even more preferably a $C_{2-4}$ dicarboxylic acid and most preferably a $C_4$ dicarboxylic acid, in particular L-tartaric acid or oxalic acid is selected such, that the final levothyroxine co-crystal dose is equivalent to a levothyroxine sodium dose of 25 microgram, 50 microgram, 75 microgram mg, 88 microgram, 100 microgram, 112 microgram, 125 microgram, 137 microgram, 150 microgram, 175 microgram, 200 microgram or 300 microgram calculated as anhydrous levothyroxine sodium.

The at least one pharmaceutically acceptable excipient, which is comprised in the pharmaceutical composition of the present invention, is preferably selected from the group consisting of fillers, diluents, binders, disintegrants, lubricants, glidants and combinations thereof.

Preferably, the pharmaceutical composition of the present invention as described above is an oral solid dosage form. In a particular preferred embodiment, the oral solid dosage form is a tablet or a capsule, most preferably a tablet.

The tablet may be prepared by mixing the co-crystal comprising levothyroxine and a dicarboxylic acid, preferably a $C_{2-8}$ dicarboxylic acid, more preferably a $C_{2-6}$ dicarboxylic acid, even more preferably a $C_{2-4}$ dicarboxylic acid and most preferably a $C_4$ dicarboxylic acid, in particular L-tartaric acid or oxalic acid with at least one excipient selected from the group consisting of fillers, diluents, binders, disintegrants, lubricants, glidants or combinations thereof. Optionally, a granulation step such as a dry or wet granulation step is performed before compression.

The capsule may be prepared by mixing the co-crystal comprising levothyroxine and a dicarboxylic acid, preferably a $C_{2-8}$ dicarboxylic acid, more preferably a $C_{2-6}$ dicarboxylic acid, even more preferably a $C_{2-4}$ dicarboxylic acid and most preferably a $C_4$ dicarboxylic acid, in particular L-tartaric acid or oxalic acid with at least one excipient selected from the group consisting of fillers, diluents, binders, disintegrants, lubricants, glidants or combinations thereof and filling the blend into a capsule. The capsule shell may be a gelatin shell or a hydroxypropylmethylcellulose (HPMC) shell.

In a further aspect, the present invention relates to a co-crystal comprising levothyroxine and a dicarboxylic acid, preferably a $C_{2-8}$ dicarboxylic acid, more preferably a $C_{2-6}$ dicarboxylic acid, even more preferably a $C_{2-4}$ dicarboxylic acid and most preferably a $C_4$ dicarboxylic acid, in particular L-tartaric acid or oxalic acid, a composition or a pharmaceutical composition comprising the same as defined in any one of the above described aspects and their corresponding embodiments for use as a medicament.

In yet another aspect, the present invention relates to a co-crystal comprising levothyroxine and a dicarboxylic acid, preferably a $C_{2-8}$ dicarboxylic acid, more preferably a $C_{2-6}$ dicarboxylic acid, even more preferably a $C_{2-4}$ dicarboxylic acid and most preferably a $C_4$ dicarboxylic acid, in particular L-tartaric acid or oxalic acid, a composition or a pharmaceutical composition comprising the same as defined in any one of the above described aspects and their corresponding embodiments for use in the treatment of hypothyroidism.

In another preferred embodiment, the invention concerns a method of treating and/or preventing hypothyroidism, said method comprising administering an effective amount of a co-crystal comprising levothyroxine and a dicarboxylic acid, preferably a $C_{2-8}$ dicarboxylic acid, more preferably a $C_{2-6}$ dicarboxylic acid, even more preferably a $C_{2-4}$ dicarboxylic acid and most preferably a $C_4$ dicarboxylic acid, in particular L-tartaric acid or oxalic acid to a patient in need of such a treatment.

EXAMPLES

The following non-limiting examples are illustrative for the disclosure and are not to be construed as to be in any way limiting for the scope of the invention.

Example 1: Preparation of the Levothyroxine L-Tartaric Acid Co-Crystal

A mixture of levothyroxine (1016 mg, 1.31 mmol), L-tartaric acid (393 mg, 2.62 mmol) and ethanol (25 mL) was stirred for 3 days with a magnetic stirrer at a speed of 250 rpm. Thereafter, the solid material was collected by filtration using a suction filter and washed with cold ethanol (~5 mL). The material was then left at room temperature on a filter paper for 0.5 h before it was further dried at room temperature under vacuum (50 mbar) for 12 h to obtain 1230 mg (yield 96% of theory) of the levothyroxine L-tartaric acid co-crystal of the present invention.

Example 2: Preparation of the Levothyroxine L-Tartaric Acid L-Lactic Acid Co-Crystal A mixture of levothyroxine (1000 mg, 1.29 mmol), L-tartaric acid (387 mg, 2.58 mmol), L-lactic acid (928 mg, 10.30 mmol) and isobutyl acetate (10 mL) was stirred with a magnetic stirrer at a speed of 250 rpm. The temperature was thereby kept in the range of from about 10 to 20° C. for about 7 days. Thereafter, the solid material was collected by filtration using a suction filter and washed twice with cold isobutyl acetate (~2×2.5 mL). The material was then left at room temperature on a filter paper for 0.5 h before it was further dried at room temperature under vacuum (50 mbar) for 12 h to obtain 1303 mg (yield 99.5% of theory) of the levothyroxine L-tartaric acid L-lactic acid co-crystal of the present invention.

Example 3: Preparation of the Levothyroxine Oxalic Acid Co-Crystal

A mixture of levothyroxine (1000 mg, 1.29 mmol), oxalic acid dihydrate (325 mg, 2.58 mmol), and ethanol (10 mL) was stirred with a magnetic stirrer at a speed of 250 rpm. The temperature was thereby kept in the range of from about 10 to 20° C. for 5 days. Thereafter, the solid material was collected by filtration using a suction filter and washed twice with cold ethanol (~2×2.5 mL). The material was then left at room temperature on a filter paper for 0.5 h before it was further dried at room temperature under vacuum (50 mbar) for 12 h to obtain 1008 mg (yield 82.5% of theory) of the levothyroxine oxalic acid co-crystal of the present invention.

Example 4: Powder X-Ray Diffraction

Powder X-ray diffractograms were obtained with an X'Pert PRO diffractometer (PANalytical, Almelo, The Netherlands) equipped with a theta/theta coupled goniometer in transmission geometry, programmable XYZ stage with well plate holder, Cu-Kalpha$_{1,2}$ radiation source (wavelength 0.15419 nm) with a focusing mirror, a 0.5° divergence slit, a 0.02° soller slit collimator and a 0.1 anti-scattering slit on the incident beam side, a 2 mm anti-scattering slit, a 0.04 soller slit collimator, a Ni-filter and a solid state PIXcel detector on the diffracted beam side. The patterns were recorded at room temperature and a tube voltage of 40 kV, tube current of 40 mA, applying a stepsize of 0.013° 2-theta with 200 sec per step in the angular range of 2° to 40° 2-Theta.

A representative diffractogram of the levothyroxine L-tartaric acid co-crystal according to the present invention is displayed in FIG. 1 and the corresponding reflection list (peak list) from 2 to 30° 2-Theta is provided in Table 1 below.

TABLE 1

Reflection (peak) positions and corresponding relative intensities of the levothyroxine L-tartaric acid co-crystal according to the present invention in the range of 2 to 30° 2-Theta; A typical precision of the 2-Theta values is in the range of ±0.2° 2-Theta, preferably of ±0.1° 2-Theta.

| Position [° 2-Theta] | Relative Intensity [%] | Position [° 2-Theta] | Relative Intensity [%] |
|---|---|---|---|
| 3.7 | 100 | 21.4 | 19 |
| 7.5 | 4 | 22.0 | 11 |
| 8.6 | 4 | 22.7 | 35 |
| 9.2 | 5 | 22.9 | 84 |
| 12.6 | 26 | 23.2 | 21 |
| 14.1 | 15 | 23.6 | 13 |
| 15.7 | 13 | 24.1 | 6 |
| 15.8 | 7 | 24.5 | 8 |
| 16.9 | 16 | 25.6 | 35 |
| 17.3 | 10 | 26.5 | 17 |
| 17.5 | 11 | 27.5 | 15 |
| 17.9 | 27 | 27.9 | 9 |
| 19.0 | 8 | 28.8 | 13 |
| 20.3 | 67 | 29.8 | 10 |
| 20.9 | 24 | | |

A representative diffractogram of the levothyroxine L-tartaric acid L-lactic acid co-crystal according to the present invention is displayed in FIG. 9 and the corresponding reflection list (peak list) from 2 to 30° 2-Theta is provided in Table 2 below.

TABLE 2

Reflection (peak) positions and corresponding relative intensities of the levothyroxine L-tartaric acid L-lactic acid co-crystal according to the present invention in the range of 2 to 30° 2-Theta; A typical precision of the 2-Theta values is in the range of ±0.2° 2-Theta, preferably of ±0.1° 2-Theta.

| Position [° 2-Theta] | Relative Intensity [%] | Position [° 2-Theta] | Relative Intensity [%] |
|---|---|---|---|
| 3.7 | 100 | 21.8 | 12 |
| 8.9 | 4 | 22.4 | 64 |
| 12.4 | 6 | 22.7 | 28 |
| 13.9 | 17 | 23.0 | 31 |
| 15.6 | 3 | 23.6 | 6 |
| 16.4 | 6 | 24.3 | 14 |
| 16.7 | 5 | 25.1 | 24 |
| 17.2 | 12 | 25.7 | 9 |
| 17.3 | 10 | 26.0 | 24 |
| 17.7 | 19 | 27.1 | 12 |
| 18.2 | 5 | 28.0 | 6 |
| 18.8 | 15 | 28.7 | 12 |
| 20.2 | 52 | 29.0 | 9 |
| 20.7 | 34 | 29.7 | 12 |
| 21.0 | 28 | | |

A representative diffractogram of the levothyroxine oxalic acid co-crystal according to the present invention is displayed in FIG. 12 and the corresponding reflection list (peak list) from 2 to 30° 2-Theta is provided in Table 3 below.

TABLE 3

Reflection (peak) positions and corresponding relative intensities of the levothyroxine oxalic acid co-crystal according to the present invention in the range of 2 to 30° 2-Theta; A typical precision of the 2-Theta values is in the range of ±0.2° 2-Theta, preferably of ±0.1° 2-Theta.

| Position [° 2-Theta] | Relative Intensity [%] | Position [° 2-Theta] | Relative Intensity [%] |
|---|---|---|---|
| 3.6 | 100 | 20.5 | 5 |
| 7.2 | 2 | 22.2 | 7 |
| 9.2 | 2 | 22.7 | 5 |
| 10.8 | 1 | 23.5 | 5 |
| 11.1 | 1 | 24.0 | 2 |
| 13.7 | 6 | 24.4 | 2 |
| 16.7 | 4 | 25.1 | 1 |
| 17.4 | 1 | 26.7 | 6 |
| 18.2 | 3 | 27.9 | 1 |
| 18.9 | 4 | 28.6 | 3 |
| 19.9 | 4 | 29.7 | 2 |

Example 5: FTIR Spectroscopy

FTIR spectra were recorded (obtained) on a MKII Golden Gate™ Single Reflection Diamond ATR cell with a Bruker Tensor 27 FTIR spectrometer with 4 cm$^{-1}$ resolution at RT. To record a spectrum a spatula tip of the sample was applied to the surface of the diamond in powder form. Then the sample was pressed onto the diamond with a sapphire anvil and the spectrum was recorded. A spectrum of the clean diamond was used as background spectrum.

A representative FTIR spectrum of the levothyroxine L-tartaric acid co-crystal according to the present invention is displayed in FIG. 2 and the corresponding peak list is provided in Table 4 below.

TABLE 4

FTIR peak list of the levothyroxine L-tartaric acid co-crystal according to the present invention; a typical precision of the wavenumbers is in the range of ±4 cm$^{-1}$, preferably of ±2 cm$^{-1}$.

| Wavenumber [cm$^{-1}$] | Wavenumber [cm$^{-1}$] |
|---|---|
| 3471 | 1221 |
| 3128 | 1185 |
| 3064 | 1150 |
| 2970 | 1128 |
| 1769 | 1079 |
| 1726 | 1037 |
| 1586 | 982 |
| 1541 | 918 |
| 1433 | 869 |
| 1400 | 822 |
| 1347 | 780 |
| 1282 | 709 |
| 1241 | 656 |

A representative FTIR spectrum of the levothyroxine L-tartaric acid L-lactic acid co-crystal according to the present invention is displayed in FIG. 10 and the corresponding peak list is provided in Table 5 below.

TABLE 5

FTIR peak list of the levothyroxine L-tartaric acid L-lactic acid co-crystal according to the present invention; a typical precision of the wavenumbers is in the range of ±4 cm$^{-1}$, preferably of ±2 cm$^{-1}$.

| Wavenumber [cm$^{-1}$] | Wavenumber [cm$^{-1}$] |
|---|---|
| 3456 | 1185 |
| 3128 | 1151 |
| 3066 | 1129 |
| 2937 | 1084 |
| 1768 | 992 |
| 1722 | 918 |
| 1588 | 890 |
| 1541 | 866 |
| 1440 | 844 |
| 1400 | 821 |
| 1349 | 779 |
| 1307 | 753 |
| 1282 | 707 |
| 1238 | 661 |
| 1224 | |

A representative FTIR spectrum of the levothyroxine oxalic acid co-crystal according to the present invention is displayed in FIG. 13 and the corresponding peak list is provided in Table 6 below.

TABLE 6

FTIR peak list of the levothyroxine oxalic acid co-crystal according to the present invention; a typical precision of the wavenumbers is in the range of ±4 cm$^{-1}$, preferably of ±2 cm$^{-1}$.

| Wavenumber [cm$^{-1}$] | Wavenumber [cm$^{-1}$] |
|---|---|
| 3466 | 1282 |
| 3066 | 1236 |
| 2971 | 1205 |
| 1726 | 1183 |
| 1631 | 1150 |
| 1585 | 1039 |
| 1518 | 914 |
| 1452 | 867 |

TABLE 6-continued

FTIR peak list of the levothyroxine oxalic acid co-crystal according to the present invention; a typical precision of the wavenumbers is in the range of ±4 cm$^{-1}$, preferably of ±2 cm$^{-1}$.

| Wavenumber [cm$^{-1}$] | Wavenumber [cm$^{-1}$] |
|---|---|
| 1432 | 841 |
| 1400 | 797 |
| 1350 | 777 |
| 1316 | 708 |

Example 6: Raman Spectroscopy

The Raman spectrum was recorded with a RamanRxn 1 Raman spectrometer and a PhAT probe with 6 mm spot size and 250 mm maximum focal length from Kaiser Optical Systems using a 785 nm Invictus laser with 400 mW power with a measurement time of 15 seconds. The spectrum was recorded from 1850 to 200 cm$^{-1}$ with 4 cm$^{-1}$ resolution at ambient conditions.

A representative Raman spectrum of the levothyroxine L-tartaric acid co-crystal according to the present invention is displayed in FIG. 3. The spectrum was clipped to 1850 to 325 cm$^{-1}$ and then baseline corrected with OPUS 7.0 (from Bruker Optik GmbH) using the concave rubberband method with 15 iterations and 64 baseline points. The corresponding peak list is provided in Table 7 below.

TABLE 7

Raman peak list of levothyroxine L-tartaric acid co-crystal according to the present invention; a typical precision of the wavenumbers is in the range of from ±4 cm$^{-1}$, preferably of from ±2 cm$^{-1}$.

| Wavenumber [cm$^{-1}$] | Wavenumber [cm$^{-1}$] | Wavenumber [cm$^{-1}$] |
|---|---|---|
| 1732 | 1242 | 780 |
| 1587 | 1185 | 754 |
| 1578 | 1056 | 724 |
| 1560 | 1041 | 611 |
| 1542 | 976 | 599 |
| 1452 | 954 | 523 |
| 1344 | 919 | 496 |
| 1314 | 881 | 381 |
| 1283 | 852 | 370 |
| 1267 | 823 | 356 |

Example 7: Single Crystal X-Ray Diffraction

Intensity data were collected at 173 K, using Mo radiation (λ=0.71073 Å), on an Oxford Diffraction Gemini-R Ultra diffractometer operated by the CrysAlisPro software (Rigaku OD, 2015). The data were corrected for absorption effects by means of comparison of equivalent reflections. The structure was solved with the direct methods procedure implemented in SHELXT and refined by full-matrix least squares on F$^2$ using SHELXL-2014. [Sheldrick, *Acta Cryst.* A71 (2015), 3-8 and C$_{71}$ (2015), 3-8]. The absolute structure was established by anomalous-dispersion effects in diffraction measurements on the crystal. A Flack x parameter of −0.05(3) was determined from 1533 quotients [(I+)−(I−)]/[(I+)+(I−)] [Parsons, Flack and Wagner, *Acta Cryst.* B69 (2013) 249-259].

Figure 4:
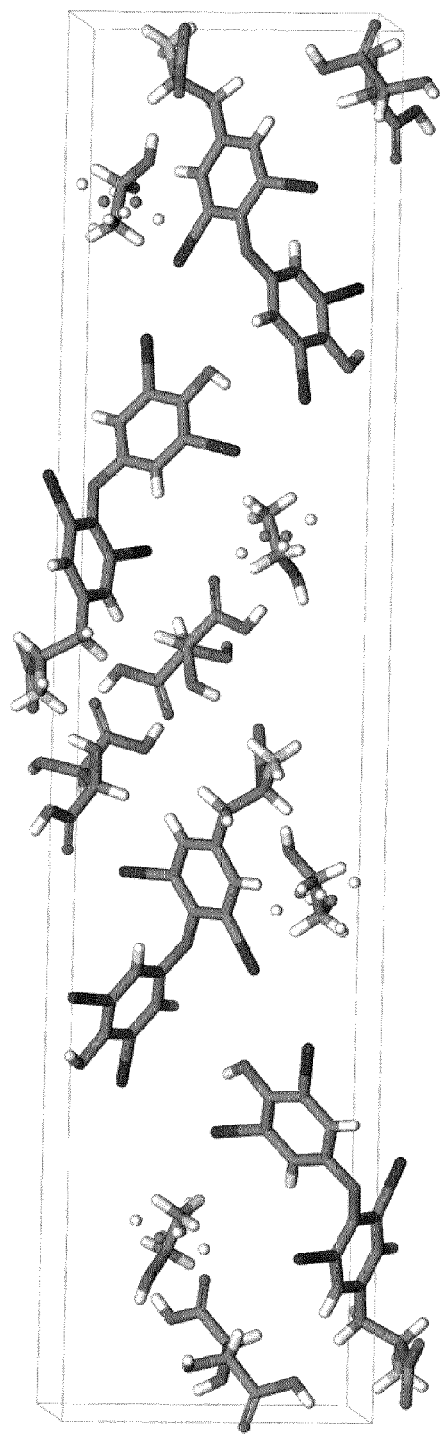
FIG. 4: illustrates the orthographic unit cell of the co-crystal of the present invention comprising levothyroxine and L-tartaric acid (view along the a-axis).

The orthographic unit cell is displayed in FIG. 4 of the present invention and the cell parameters are provided in Table 8 below.

TABLE 8

Cell parameters of the levothyroxine L-tartaric acid co-crystal of the present invention

| | |
|---|---|
| Moiety formula | C$_{15}$ H$_{11}$ I$_4$ O$_4$N•C$_4$H$_6$O$_6$•C$_2$H$_6$O |
| Temperature | 173(2) K |
| Crystal system | Orthorhombic |
| Space group | P 2$_1$ 2$_1$ 2$_1$ |
| Unit cell dimension | a = 5.7600(4) Å |
| | b = 10.4551(5) Å |
| | c = 46.8620(18) Å |
| | α = 90° |
| | β = 90° |
| Volume | 2822.09 Å$^3$ |
| Z/Z' | 4/1 |
| Data/restraints/parameters | 5327/13/360 |
| Goodness-of-fit on F$^2$ | 1.025 |
| Final R indices [I > 2σ(I)] | R1 = 0.0473, wR2 = 0.0732 |
| R indices (all data) | R1 = 0.0638, wR2 = 0.0785 |
| Absolute structure parameter | −0.05(3) |

The structure obtained from single crystal X-ray diffraction suggests that the levothyroxine L-tartaric acid co-crystal of the present invention is a 3 component crystal system comprising levothyroxine, L-tartaric acid and ethanol in the unit cell in the same molar ratios. The intermolecular interactions are based on hydrogen bondings and are therefore of non-ionic nature. The levothyroxine L-tartaric co-crystal according to the present invention can therefore be assigned as levothyroxine L-tartaric acid cocrystal ethanol solvate, more precisely as levothyroxine L-tartaric acid co-crystal monoethanol solvate.

Comparative Example 1: Thermal Stability (DSC)

The levothyroxine L-tartaric acid co-crystal as well as the levothyroxine L-tartaric acid L-lactic acid co-crystal according to the present invention and commercial levothyroxine sodium pentahydrate were investigated by DSC, which was performed with a DSC 7 (Perkin-Elmer, Norwalk, Ct., USA) using a Pyris 2.0 software. Each sample (approximately 4±0.0005 mg using a UM3 ultramicrobalance, Mettler, Greifensee, CH) was weighed into an aluminum pan (25 microlitre) and sealed with a cover, which was perforated by a needle. Dry nitrogen was used as the purge gas (purge rate: 20 mL/min). The samples were heated from 20 to 235° C. at a heating rate of 20 K/min.

Figure 5:
FIG. 5: illustrates representative TGA (top) and DSC (bottom) curves in the range of 30 to 230° C. of the co-crystal of the present invention comprising levothyroxine and L-tartaric acid. The x-axis shows the temperature in degree Celsius (° C.). The left y-axis shows the heat flow rate in milli Watt (mW) with endothermic peaks going up. The right y-axis shows the mass (loss) of the sample in weight percent (weight %).

The DSC curve of the levothyroxine L-tartaric acid co-crystal of the present invention, which is displayed at the bottom of FIG. 5 herein, shows a first endothermic peak with an onset temperature of about 149° C. and a peak maximum temperature of about 165° C., which is due to a desolvation process caused by the loss of ethanol. The second endothermic peak with an onset temperature of about 180° C. and a peak maximum temperature of about 197° C. is due to a concomitant melting and decomposition process.

Figure 11:
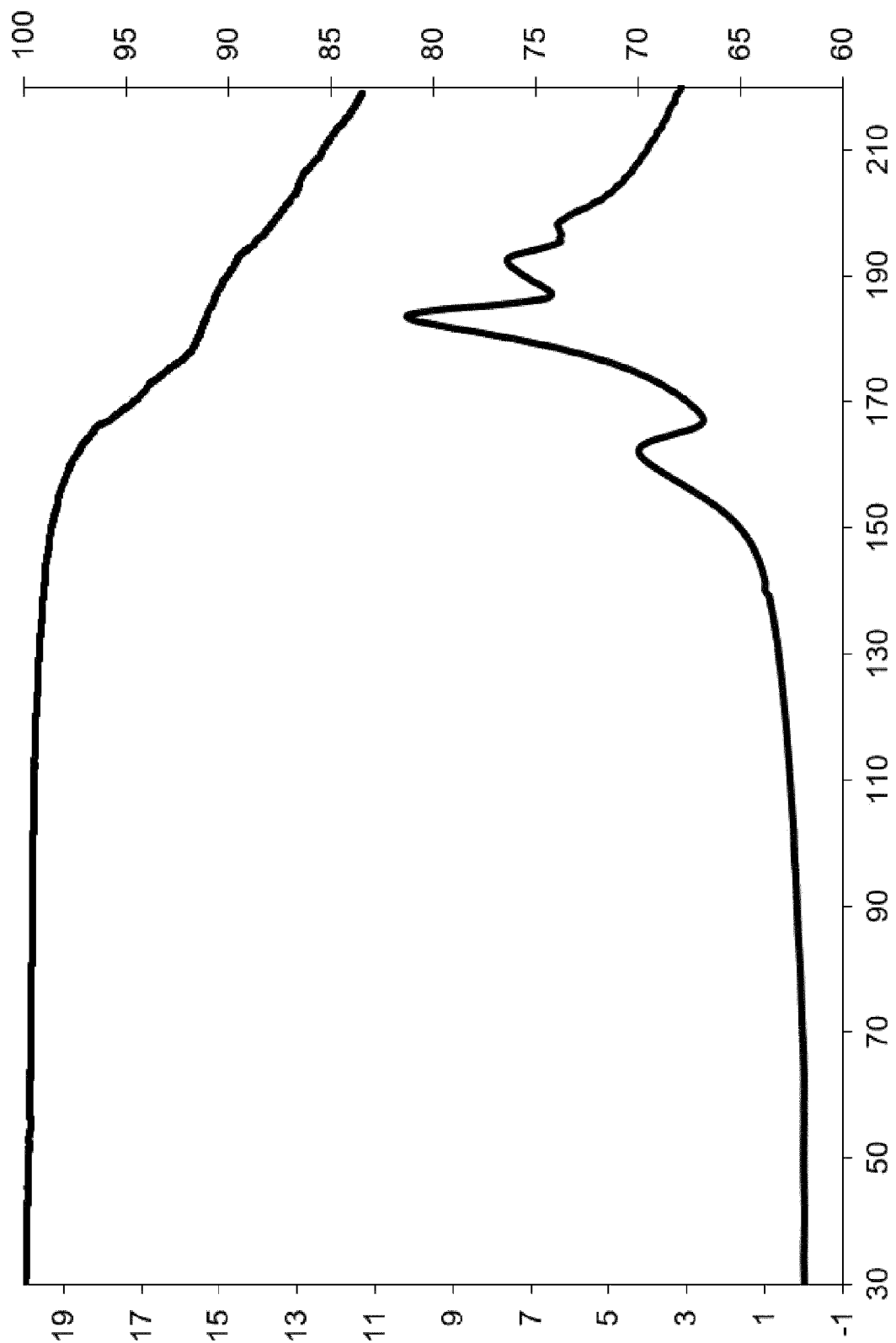
FIG. 11: illustrates representative TGA (top) and DSC (bottom) curves in the range of 30 to 230° C. of the co-crystal of the present invention comprising levothyroxine, L-tartaric acid and L-lactic acid. The x-axis shows the temperature in degree Celsius (° C.). The left y-axis shows the heat flow rate in milli Watt (mW) with endothermic peaks going up. The right y-axis shows the mass (loss) of the sample in weight percent (weight %).

The DSC curve of the levothyroxine L-tartaric acid L-lactic acid co-crystal of the present invention, which is displayed at the bottom of FIG. 11 herein, shows a first endothermic peak with an onset temperature of about 151° C. and a peak maximum temperature of about 162° C., which is due to the release of lactic acid. In addition, a peak with a maximum at about 183° C. indicates a melting process before the sample undergoes decomposition.

Figure 6:
FIG. 6: illustrates representative TGA (top) and DSC (bottom) curves in the range of 30 to 230° C. of levothyroxine sodium pentahydrate. The x-axis shows the temperature in degree Celsius (° C.). The left y-axis shows the heat flow rate in milli Watt (mW) with endothermic peaks going up. The right y-axis shows the mass (loss) of the sample in weight percent (weight %).

The DSC curve of commercial levothyroxine sodium pentahydrate, which is displayed at the bottom of FIG. 6 herein shows a broad endothermic peak with an onset temperature of about 53° C. and multiple peak maxima at temperatures of about 78° C., 106° C. and 116° C. This signal is due to dehydration caused by the loss of crystal water. The sample exhibits an exothermic peak with an onset temperature of about 202° C. and a peak maximum temperature of about 205° C., which is due to decomposition.

DSC analysis revealed that the levothyroxine L-tartaric acid co-crystal of the present invention is more stable against temperature stress and desolvates significantly later compared to levothyroxine sodium pentahydrate, which starts to lose its crystal water already at relatively low temperature. Also the levothyroxine L-tartaric acid L-lactic acid co-crystal of the present invention is more stabe against temperature stress compared to levothyroxine sodium pentahydrate. E.g. the levothyroxine L-tartaric acid L-lactic acid co-crystal of the present invention only starts to lose L-lactic acid at about 151° C.

TABLE 9

Desolvation events observed in DSC experiments

| Levothyroxine | Thermal event | $T_{onset}$ | $T_{peak}$ |
|---|---|---|---|
| L-tartaric acid co-crystal | desolvation (loss of EtOH) | 149° C. | 165° C. |
| sodium pentahydrate | dehydration (loss of $H_2O$) | 53° C. | 78° C., 106° C., 116° C. |
| L-tartaric acid L-lactic acid co-crystal | loss of lactic acid | 151° C. | 162° C. |

Comparative Example 2: Thermal Stability (TGA)

The levothyroxine L-tartaric acid co-crystal as well as the levothyroxine L-tartaric acid L-lactic acid co-crystal of the present invention and commercial levothyroxine sodium pentahydrate were investigated by TGA, which was performed on a thermogravimetric system TGA-1 using a Pyris software for Windows NT (Perkin-Elmer, Norwalk, Ct., USA). Each sample (approximately 4±0.0005 mg using a UM3 ultramicrobalance, Mettler, Greifensee, CH) was weighed into an unsealed platinum sample holder (50 microlitre). The samples were heated from 20 to 235° C. at a rate of 10 K/min. Nitrogen (sample purge rate 20 mL/min and balance purge rate 40 mL/min)) was used as purge gas.

The TGA curve of the levothyroxine L-tartaric acid co-crystal of the present invention, which is displayed at the top of FIG. 5 herein, shows only a slight mass loss up to a temperature of about 120° C. Only at temperatures between about 150 to 170° C. a distinct step in the TGA curve appears, which corresponds well to the endotherm observed in the DSC curve shown on the bottom of FIG. 5 and can therefore be assigned to the desolvation process.

The TGA curve of the levothyroxine L-tartaric acid L-lactic acid co-crystal of the present invention, which is displayed at the top of FIG. 11 herein, shows only a slight mass loss of about 0.5 weight-% up to a temperature of about 120° C. Only at temperatures between about 150 to 170° C. a distinct step in the TGA curve appears, which corresponds well to the first endothermic peak observed in the DSC curve shown on the bottom of FIG. 11 and can be assigned to the release of lactic acid.

The TGA curve of commercial levothyroxine sodium pentahydrate, which is displayed at the top of FIG. 6 herein, shows a significant weight loss from the beginning of the measurement until about 120° C., which corresponds well to the endotherm observed in the DSC curve shown on the bottom of FIG. 6 and can therefore be assigned to the dehydration process.

TABLE 10

Desolvation events observed in TGA experiments

| Levothyroxine | Thermal event | Temperature range |
|---|---|---|
| L-tartaric acid co-crystal | desolvation (loss of EtOH) | ~150-170° C. |
| sodium pentahydrate | dehydration (loss of $H_2O$) | ~30-120° C. |
| L-tartaric acid L-lactic acid co-crystal | release of lactic acid | ~150-170° C. |

Comparative Example 3: Chemical Stability

The levothyroxine L-tartaric acid co-crystal, the levothyroxine L-tartaric acid L-lactic acid cocrystal as well as the levothyroxine oxalic acid co-crystal of the present invention and commercial levothyroxine sodium pentahydrate were exposed to ambient air (oxygen concentration of about 20.9 volume %) at a temperature of 40° C. and a relative humidity of 0% for a period of 6 weeks. A $^1$H-NMR spectrum of each substance was recorded at the beginning of the test period, at 3 weeks and finally at 6 weeks. Spectra were recorded on a Bruker Avance-300 Spectrometer (Spectrometer frequency: 300 MHz). Each sample for analysis was prepared by dissolving about 20 mg of solid in 600 microlitres of $d_6$-DMSO. All samples were analysed immediately after preparation.

Figure 7:
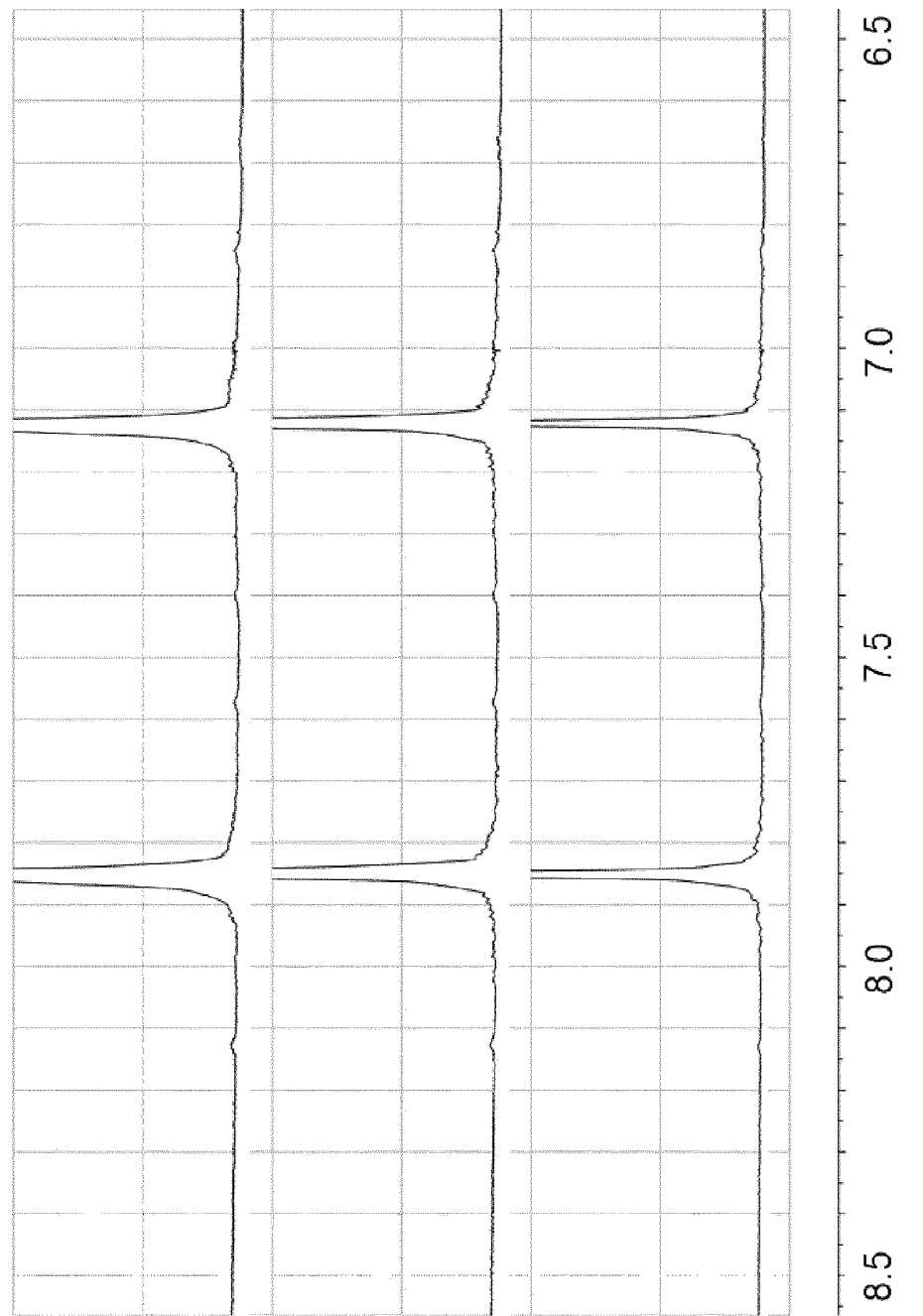
FIG. 7: illustrates a stack plot of $^1$H-NMR spectra of the co-crystal of the present invention comprising levothyroxine and L-tartaric acid of the initial sample (bottom), the sample exposed for 3 weeks (middle) and the sample exposed for 6 weeks (top) to ambient molecular oxygen at 0% RH and 40° C. The x-axis shows the chemical shifts in parts per million (ppm) in the range of 6.5 to 8.5 ppm.

FIG. 7 shows a stack plot of the $^1$H-NMR spectra of the initial levothyroxine L-tartaric acid co-crystal (bottom) and the stressed sample after 3 weeks (middle) and after 6 weeks (top). According to the $^1$H-NMR spectra, the levothyroxine L-tartaric acid co-crystal of the present invention remains chemically stable under the applied stress conditions.

Figure 8:
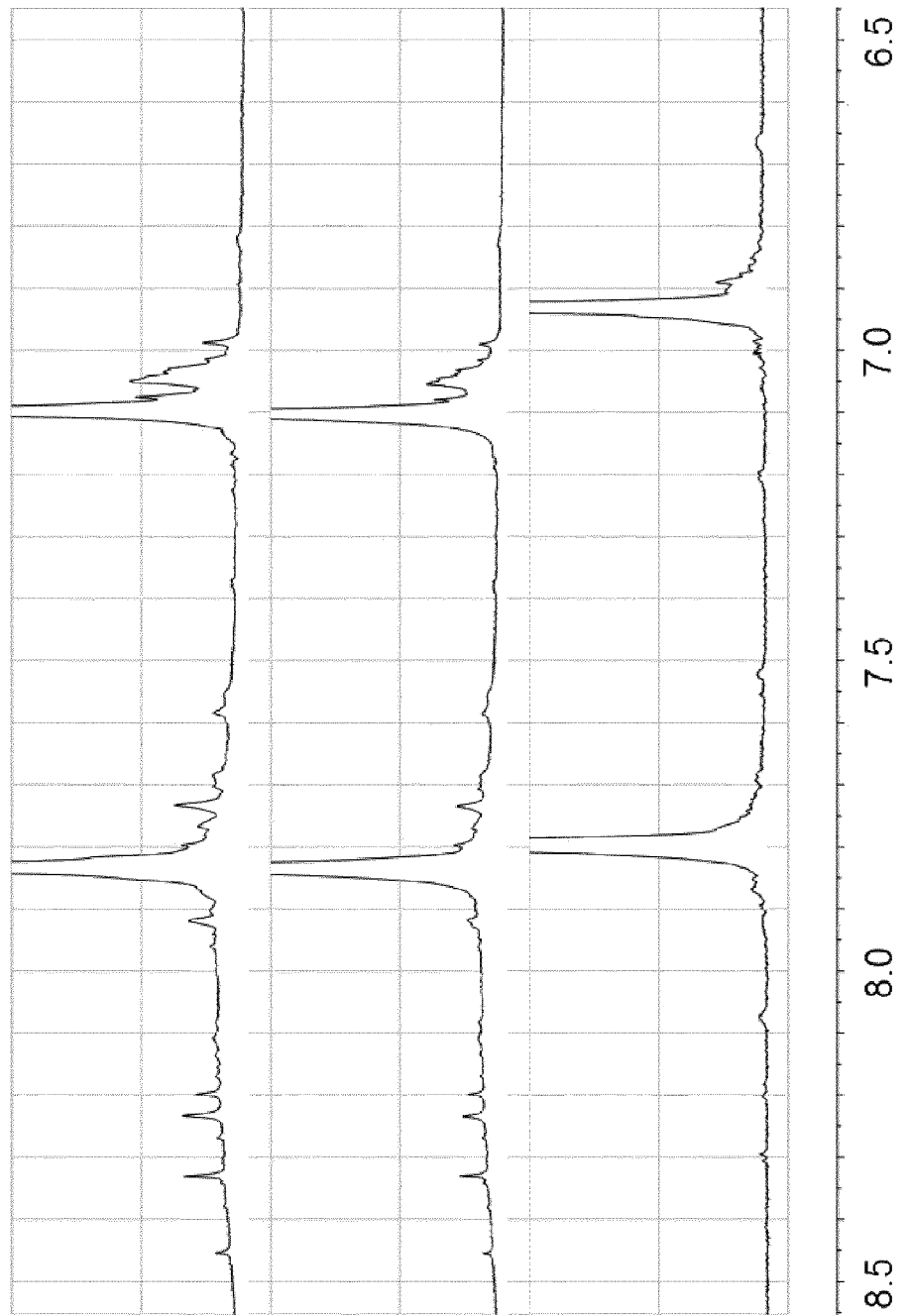
FIG. 8: illustrates a stack plot of $^1$H-NMR spectra of levothyroxine sodium pentahydrate of the initial sample (bottom), the sample exposed for 3 weeks (middle) and the sample exposed for 6 weeks (top) to ambient molecular oxygen at 0% RH and 40° C. The x-axis shows the chemical shifts in parts per million (ppm) in the range of 6.5 to 8.5 ppm.

FIG. 8 shows a stack plot of the $^1$H-NMR spectra of the initial levothyroxine sodium pentahydrate (bottom) and the stressed sample after 3 weeks (middle) and after 6 weeks (top). After 3 weeks under the applied stress conditions, additional peaks become evident in the $^1$H-NMR spectrum of levothyroxine sodium pentahydrate, which become even more intense after 6 weeks. Hence, levothyroxine sodium pentahydrate is chemically unstable under the applied stress conditions.

FIG. 14 shows a stack plot of the $^1$H-NMR spectra of the initial levothyroxine L-tartaric acid L-lactic acid co-crystal (bottom) and the stressed sample after 3 weeks (middle) and after 6 weeks (top). According to the $^1$H-NMR spectra, the levothyroxine L-tartaric acid L-lactic acid co-crystal of the present invention remains chemically stable under the applied stress conditions.

FIG. 15 shows a stack plot of the $^1$H-NMR spectra of the initial levothyroxine oxalic acid co-crystal (bottom) and the stressed sample after 3 weeks (middle) and after 6 weeks (top). According to the $^1$H-NMR spectra, the levothyroxine oxalic acid co-crystal of the present invention remains chemically stable under the applied stress conditions.

The invention claimed is:

1. Co-crystal comprising levothyroxine and a dicarboxylic acid selected from the group consisting of tartaric acid and oxalic acid.

2. The co-crystal of claim 1, wherein the dicarboxylic acid is L-tartaric acid.

3. The co-crystal comprising levothyroxine and L-tartaric acid of claim 2 characterized by having a powder X-ray diffractogram comprising reflections at 2-Theta angles of (3.7±0.2)°, (20.3±0.2)° and (22.9±0.2)°, when measured at a temperature in the range of from 20 to 30° C. with Cu-Kalpha$_{1,2}$ radiation having a wavelength of 0.15419 nm.

4. The co-crystal of claim 3 characterized by having a powder X-ray diffractogram comprising additional reflections at 2-Theta angles of (12.6±0.2)° and/or (17.9±0.2)°, when measured at a temperature in the range of from 20 to 30° C. with Cu-Kalpha$_{1,2}$ radiation having a wavelength of 0.15419 nm.

5. The co-crystal of claim 2 characterized by having an FTIR spectrum comprising peaks at (3471±4) cm$^{-1}$, (1769±4) cm$^{-1}$, (1586±4) cm$^{-1}$, (1433±4) cm$^{-1}$ and (1221±4) cm$^{-1}$, when measured at temperature in the range of from 20 to 30° C. with a diamond ATR cell.

6. The co-crystal of claim 2 characterized by having a Raman spectrum comprising peaks at wavenumbers of (1732±4) cm$^{-1}$, (1587±4) cm$^{-1}$, (1242±4) cm$^{-1}$, (1056±4) cm$^{-1}$ and (823±4) cm$^{-1}$, when measured at a temperature in the range of from 20 to 30° C. and a wavelength of 785 nm.

7. The co-crystal of claim 2, wherein the molar ratio of levothyroxine and L-tartaric acid is in the range of from 1.0:0.8-1.2.

8. The co-crystal of claim 2 characterized as being an ethanol solvate.

9. The co-crystal of claim 8, wherein the molar ratio of levothyroxine, L-tartaric acid and ethanol is in the range of from 1.0:0.8-1.2:0.8-1.2.

10. The co-crystal comprising levothyroxine and L-tartaric acid of claim 2 further comprising L-lactic acid.

11. The co-crystal of claim 10 characterized by having a powder X-ray diffractogram comprising reflections at 2-Theta angles of (3.7±0.2)°, (20.2±0.2)° and (22.4±0.2)°, when measured at a temperature in the range of from 20 to 30° C. with Cu-Kalpha$_{1,2}$ radiation having a wavelength of 0.15419 nm.

12. The co-crystal of claim 11 characterized by having a powder X-ray diffractogram comprising additional reflections at 2-Theta angles of (13.9±0.2)° and/or (20.7±0.2)°, when measured at a temperature in the range of from 20 to 30° C. with Cu-Kalpha$_{1,2}$ radiation having a wavelength of 0.15419 nm.

13. The co-crystal of claim 10 characterized by having an FTIR spectrum comprising peaks at (3456±4) cm$^{-1}$, (1768±4) cm$^{-1}$, (1440±4) cm$^{-1}$, (1238±4) cm$^{-1}$ and (1084±4) cm$^{-1}$, when measured at temperature in the range of from 20 to 30° C. with a diamond ATR cell.

14. The co-crystal of claim 10, characterized by having a molar ratio of levothyroxine, L-tartaric acid and L-lactic acid in the range of from 1.0:0.8-1.2:0.8-1.2.

15. The co-crystal of claim 1, wherein the dicarboxylic acid is oxalic acid.

16. The co-crystal of claim 15 characterized by having a powder X-ray diffractogram comprising reflections at 2-Theta angles of (3.6±0.2)°, (13.7±0.2)° and (22.2±0.2)°, when measured at a temperature in the range of from 20 to 30° C. with Cu-Kalpha$_{1,2}$ radiation having a wavelength of 0.15419 nm.

17. The co-crystal of claim 16, characterized by having a powder X-ray diffractogram comprising additional reflections at 2-Theta angles of (16.7±0.2)° and/or (20.5±0.2)°, when measured at a temperature in the range of from 20 to 30° C. with Cu-Kalpha$_{1,2}$ radiation having a wavelength of 0.15419 nm.

18. The co-crystal of claim 15, wherein the molar ratio of levothyroxine and oxalic acid is in the range of from 1.0:0.8-1.2.

19. The co-crystal of claim 15, characterized as being an ethanol solvate.

20. The co-crystal of claim 19, wherein the molar ratio of levothyroxine, oxalic acid and ethanol is in the range of from 1.0:0.8-1.2:0.8-1.2.

21. A pharmaceutical composition comprising a co-crystal as defined in claim 1 and at least one pharmaceutically acceptable excipient.

22. The pharmaceutical composition according to claim 21, wherein the pharmaceutical composition is an oral solid dosage form.

23. The pharmaceutical composition of claim 22, wherein the oral solid dosage form is a tablet or a capsule.

24. A method of treatment and/or prophylaxis of hypothyroidism, comprising the step of administering to a patient in need of such treatment the pharmaceutical composition according to claim 21.

25. A method for preparing a pharmaceutical composition comprising the co-crystal as defined in claim 1, comprising the steps of
(i) providing the co-crystal as defined in claim 1;
(ii) providing at least one pharmaceutically acceptable excipient; and
(iii) preparing said pharmaceutical composition from (i) and (ii).

26. The method of claim 25, wherein the pharmaceutical composition is an oral solid dosage form.

27. The method of claim 26, wherein the oral solid dosage form is a tablet or a capsule.

* * * * *